US009322055B2

(12) United States Patent
Janaway et al.

(10) Patent No.: US 9,322,055 B2
(45) Date of Patent: Apr. 26, 2016

(54) SYSTEM AND METHOD FOR DETERMINING COPIES-PER-UNIT-VOLUME USING PCR AND FLOW CONTROL OF DROPLETS

(75) Inventors: Gordon A. Janaway, Hayward, CA (US); Mark Andersen, Carlsbad, CA (US); Kornelija Zgonc, Carlsbad, CA (US); Michael Pallas, San Bruno, CA (US); Marcin Sikora, Foster City, CA (US); Casey McFarland, San Francisco, CA (US); Ferrier N. Le, San Jose, CA (US); Haopeng Wang, Carlsbad, CA (US); Jian Gong, San Marcos, CA (US); Gothami Padmabandu, San Diego, CA (US)

(73) Assignee: Life Technologies Corporation, Carlsbad, CA (US)

(*) Notice: Subject to any disclaimer, the term of this patent is extended or adjusted under 35 U.S.C. 154(b) by 47 days.

(21) Appl. No.: 14/009,304

(22) PCT Filed: Mar. 30, 2012

(86) PCT No.: PCT/US2012/031533
§ 371 (c)(1),
(2), (4) Date: Oct. 1, 2013

(87) PCT Pub. No.: WO2012/135667
PCT Pub. Date: Oct. 4, 2012

(65) Prior Publication Data
US 2014/0248623 A1 Sep. 4, 2014

Related U.S. Application Data

(60) Provisional application No. 61/470,713, filed on Apr. 1, 2011, provisional application No. 61/481,085, filed on Apr. 29, 2011.

(51) Int. Cl.
*C12Q 1/68* (2006.01)
*C12P 19/34* (2006.01)

(52) U.S. Cl.
CPC ..................... *C12Q 1/686* (2013.01)

(58) Field of Classification Search
CPC .............. C12Q 1/686; C12Q 2537/16; C12Q 2563/143; C12Q 2563/159; C12Q 2565/626
See application file for complete search history.

(56) References Cited

U.S. PATENT DOCUMENTS

2005/0042639 A1* 2/2005 Knapp et al. ..................... 435/6

FOREIGN PATENT DOCUMENTS

| WO | 98/47003 | 10/1998 |
|---|---|---|
| WO | 2007/024798 | 3/2007 |
| WO | 2007/149432 | 12/2007 |
| WO | 2010/117461 | 10/2010 |

OTHER PUBLICATIONS

Kojima et al., "PCR amplification from single DNA molecules on magnetic beads in emulsion: application for high-throughput screening of transcription factor targets," Nucleic Acids Research, 2005, vol. 33, No. 17, e150, pp. 1-9.*
International Search Report and Written Opinion of the ISA for International Appl. No. PCT/US2012/031533 dated Jun. 12, 2012.
Curcio, Mario et al., "Continuous segmented-Flow Polymerase Chain Reaction for High-Throughput Miniaturized DNA Amplification", *Anal. Chem*, vol. 75(1), American Chemical Society, 2003, 1-7.
Dorfman, Kevin D. et al., "Contamination-free Continuous Flow Microfluidic Polymerase Chain Reaction for Quantitative and Clinical Applications", *Analytical Chemistry, American Chemical Society*, vol. 77, No. 11, Jun. 2005, 3700-3704.

* cited by examiner

*Primary Examiner* — Young J Kim

(57) ABSTRACT

Methods and systems for quantification of a target nucleic acid in a sample are provided. The method includes forming a plurality of discrete sample portions. Each of the plurality of discrete sample portions comprising a portion of the sample, and a reaction mixture. The method further includes amplifying the plurality of discrete sample portions to form a plurality of discrete processed sample portions. At least one discrete processed sample portion containing nucleic acid amplification reaction products. Fluorescence signals are detected from the at least one of the plurality of discrete processed sample portions to determine a presence of the at least one target nucleic acid. The method also includes determining the respective volumes of the plurality of the plurality of discrete processed sample portions, and estimating the number of copies-per-unit-volume of the at least one target nucleic acid in the sample. Estimating the number of copies-per-unit-volume is based on the number of discrete processed sample portions determined to contain the at least one target nucleic acid therein.

22 Claims, 34 Drawing Sheets

SYSTEM AND METHOD FOR DETERMINING COPIES-PER-UNIT-VOLUME USING PCR AND FLOW CONTROL OF DROPLETS

CROSS-REFERENCE TO RELATED APPLICATIONS

This application is a National Stage entry from PCT Application No. PCT/US2012/031533 filed Mar. 30, 2012, which claims a benefit under 35 USC §119(e) from U.S. Provisional Application Nos. 61/470,713, filed Apr. 1, 2011, and 61/481,085, filed Apr. 29, 2011; all applications are incorporated herein by reference in their entirety.

BACKGROUND

The present disclosure generally relates to systems and methods for carrying out digital polymerase chain reaction (dPCR) assays. The disclosure further relates to controlling the flow of droplets dispersed in a carrier fluid through a conduit.

Digital Polymerase Chain Reaction (dPCR) is a method that has been described, for example, in U.S. Pat. No. 6,143,496 to Brown et al. Results from dPCR can be used to detect and quantify the concentration of rare alleles, to provide absolute quantitation of nucleic acid samples, and to measure low fold-changes in nucleic acid concentration.

dPCR is often performed using apparatus adapted from conventional qPCR, in which replicates are arrayed in a two dimensional array format including m rows by n columns, i.e., an m×n format. PCR cycling and read-out (end-point or real-time) generally occurs within the same array. A maximum of m×n replicates can be processed in a single batch run. Generally, increasing the number of replicates increases the accuracy and reproducibility of dPCR results.

The (m×n) format in most quantitative polymerase chain reaction (qPCR) platforms is designed for sample-by-assay experiments, in which PCR results need to be addressable for post-run analysis. For dPCR, however, the specific position or well of each PCR result may be immaterial and only the number of positive and negative replicates per sample may be analyzed.

The read-out of dPCR, that is, the number of positive reactions and the number of negative reactions, is linearly proportional to the template concentration, while the read-out of qPCR (signal vs. cycle) is proportional to the log of the template concentration. For this reason, dPCR typically is constrained to a narrow dynamic range of template input.

SUMMARY

According to various embodiments, the present teachings provide methods and systems for quantification of a target nucleic acid in a sample. The method includes forming a plurality of discrete sample portions. Each of the plurality of discrete sample portions comprising a portion of the sample, and a reaction mixture. The method further includes amplifying the plurality of discrete sample portions to form a plurality of discrete processed sample portions. At least one discrete processed sample portion containing nucleic acid amplification reaction products. Fluorescence signals are detected from the at least one of the plurality of discrete processed sample portions to determine a presence of the at least one target nucleic acid. The method also includes determining the respective volumes of the plurality of the plurality of discrete processed sample portions, and estimating the number of copies-per-unit-volume of the at least one target nucleic acid in the sample. Estimating the number of copies-per-unit-volume is based on the number of discrete processed sample portions determined to contain the at least one target nucleic acid therein.

In some embodiments, the plurality of discrete sample portions may comprise sample portions of different sizes or all of the same size. Each of the plurality of discrete sample portions may comprise a volume of an aqueous reaction medium at least partially surrounded by a medium that is at least substantially immiscible with the plurality of discrete sample portions. As used herein, sample portions may be referred to as droplets, sample volumes, or reactions volumes, for example. The medium that is substantially immiscible with the plurality of discrete sample portions may comprise one or more of a mineral oil, a silicone oil, a paraffin oil, a fluorinated fluid, a perfluorinated polyether, and a combination thereof. In some embodiments, the plurality of discrete sample portions comprise magnetic beads and the method may further comprise magnetically focusing the magnetic beads within a flow stream in a flow cytometer. In some embodiments, the plurality of sample portions may comprise non-magnetic beads, including porous or hollow beads, for example. The porous or hollow beads may be spherical or cylindrical. One or more of the plurality of sample portions may comprise a passive reference dye, a light-scattering enhancing material, q-dots, a protein, a colloidal metal, colloidal gold, a reporter dye, a reaction-independent flow marker, or a combination thereof. In some embodiments, one or more sample discrete portions of the plurality of sample portions comprises a primer pair, a nucleotide probe, and a Taq polymerase.

In another embodiment, a system for quantification of a target nucleic acid in a sample is provided. The system includes an emulsion apparatus configured to form a plurality of discrete sample portions. Each of the plurality of discrete sample portions includes a portion of the sample, and a reaction mixture. The system further includes an amplification apparatus configured to amplify the plurality of discrete sample portions to form a plurality of discrete processed sample portions, including at least one discrete processed sample portion containing nucleic acid amplification reaction products. The system also includes excitation detection apparatus configured to detect fluorescence signals from the at least one of the plurality of discrete processed sample portions to determine a presence of the at least one target nucleic acid. Furthermore, the system includes a processor configured to estimate the number of copies-per-unit-volume of the at least one target nucleic acid in the sample based on the number of discrete processed sample portions determined to contain the at least one target nucleic acid therein.

BRIEF DESCRIPTION OF THE DRAWINGS

A better understanding of the features and advantages of the present disclosure will be obtained by reference to the accompanying drawings, which are intended to illustrate, not limit, the present teachings.

DETAILED DESCRIPTION

Figure 1:
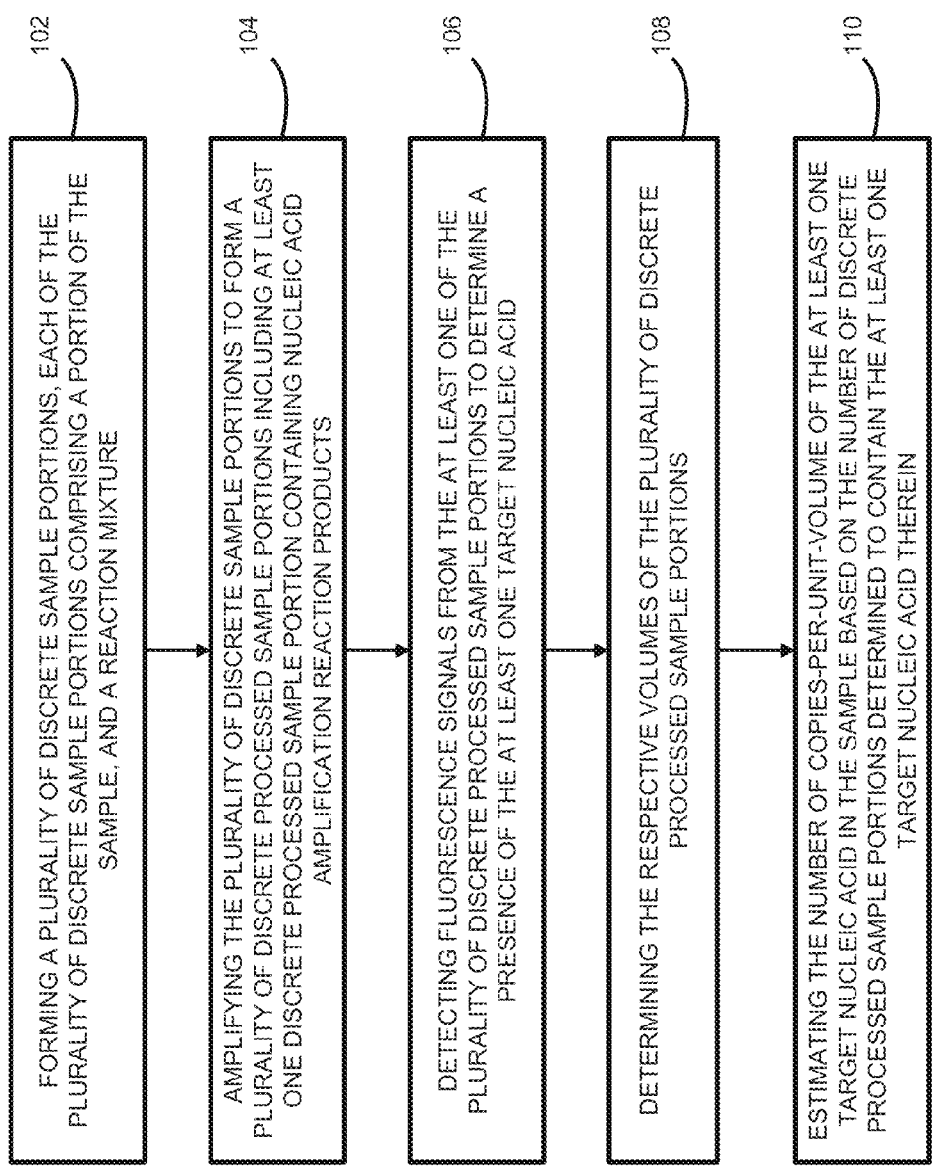
FIG. 1 is a flow diagram of an exemplary method according to various embodiments of the present teachings.

The systems and methods described herein provides a dPCR system and method that does not rely on the fixed (m×n) format and instead uses droplet flow control to greatly increases the number of dPCR replicates that can be obtained while also obtaining a tally of positive and negative results useful for dPCR. Unlike fixed format approaches, the accuracy and precision of the dPCR result can be tuned as desired, simply by varying the observation time and flow rate to obtain the required number of replicates.

In various embodiments, the methods and systems described herein may be used to detect other biological components of interest. These biological components of interest may be any suitable biological target including, but are not limited to, DNA sequences (including cell-free DNA), RNA sequences, genes, oligonucleotides, molecules, proteins, biomarkers, cells (e.g., circulating tumor cells), or any other suitable target biomolecule.

Furthermore, in addition to dPCR, the methods and systems in various embodiments may be used in applications, such as fetal diagnostics, PCR, qPCR, dPCR, allele-specific PCR, asymmetric PCR, ligation-mediated PCR, multiplex dPCR, nested PCR, bridge PCR, genome walking, viral detection and quantification standards, genotyping, sequencing validation, mutation detection, detection of genetically modified organisms, rare allele detection, and copy number variation.

As used herein, droplets may be referred to as sample portions, sample volumes, or reactions volumes, for example.

In some embodiments, a flow cytometer, for example, an acoustic flow cytometer can be used to control the flow of aqueous droplets dispersed in a substantially immiscible carrier fluid, through a conduit.

According to various embodiments, analysis of a sample may include preparing uniform or variously-sized sample portions. The sample portions are amplified so that the sample portions contain the target nucleic acid. Amplification may be performed by polymerase chain reactions (PCR) with target concentration near terminal dilution. According to various embodiments, amplification may also be performed by isothermal amplification, thermal convention, infrared mediated thermal cycling, or helicase dependent amplification, for example.

According to various embodiments, detection of a target may be, but is not limited to, fluorescence detection, detection of positive or negative ions, pH detection, voltage detection, or current detection, alone or in combination, for example.

The volume of the sample portions may be known. If the sample portions are different sizes, the volume of the sample portions may need to be determined. The positive and negative reactions within the plurality of sample portions are counted. More particularly, the number of sample portions that contain successful amplification of the target nucleic acid are counted. The sizes and the positive and negative reactions may be determined by imaging, for example. The average copy number per reaction is estimated. The estimation may be made using a Poisson distribution. Then, the target copy number per unit volume in the starting sample is estimated. This exemplary method is generally shown in the flow chart depicted in FIG. 1.

As shown in FIG. 1, the method may comprise forming a plurality of discrete sample portions in step 102. Each of the plurality of a discrete sample portions may include a portion of the sample, and reaction reagents, such as PCR reagents. The sample may also be diluted. In some embodiments the plurality of discrete sample portions may be reactor droplets. The plurality of discrete sample portions may also be porous beads or magnetic beads, for example. The discrete sample portions may be a plurality of sizes, a uniform size, or different predetermined sizes.

The method may further comprise amplification of the plurality of discrete sample portions to form a plurality of processed sample portions in step 104. At least one of the plurality of discrete processed sample portions contain nucleic acid amplification reaction products. The amplification may be by subjecting the reactor droplets to thermal cycling in various embodiments.

Then, the method may include detecting fluorescence signals from the processed sample portions to determine a presence of at least one target nucleic acid, as in step 106. In other words, the plurality of discrete processed sample portions may be determined to be positive or negative for amplification. According to various embodiments, detection of a target may be, but is not limited to, fluorescence detection, detection of positive or negative ions, pH detection, voltage detection, or current detection, alone or in combination, for example.

The method further includes determining the respective volumes of the plurality of discrete processed sample portions in step 108. The volumes may be determined from imaging the plurality of discrete processed sample portions. In various embodiments, the imaging may be done by positioning the plurality of discrete sample portions in the field of view of an imaging apparatus. This may be used where the plurality of discrete sample portions are a plurality of sizes, which may be referred to as a polydisperse emulsion. In other embodiments, the discrete sample portions may be of a uniform size and the volume may be known. In yet other embodiments, the discrete sample portions may be a known number of different sizes, which may be referred to as an multi-mono dispersed emulsion. For example, the discrete sample portions may be two different sizes. In other embodiments, the discrete sample portions may be three different sizes, for example. In this way, by determining which size each of the plurality of discrete sample portions is, the volume may be determined.

According to various embodiments, a method is provided to create monodisperse reverse emulsions using T-junctions, as described for example, in U.S. Patent Application Publication No. US 2007/0141593 A1 to Lee et al., which is incorporated herein in its entirety by reference. There would thus be no need to estimate the size of the discrete sample portions. Some or all of these workflow steps may be integrated into a single closed system.

The polydisperse emulsions achieved by the present systems and methods are relatively easy and cheap to make, and do not require a consumable. Due to the difference in volume of the discrete sample portions volumes, they create approximately 3OM greater dynamic range of sample input for dPCR without sample dilution. Acoustic focusing allows massive droplet throughput and low shear stress to stabilize the plurality of discrete sample portions in a flow. Also, acoustic focusing has flow speed flexibility that allows a significant signal to noise increase by varying flow speeds. This process allows very high numbers of discrete sample portions to be read, increasing the accuracy, precision, and dynamic range of dPCR.

The method may further include estimating the number of target template copies-per-unit-volume of the at least one target nucleic acid in the sample based on the number of discrete processed sample portions determined to contain the at least one target nucleic acid there, in step 110. As such, the quantity of the target nucleic acid may be determined.

In various embodiments, the method may also comprise averaging the results to improve accuracy and precision and/or estimating the target copy number per unit volume in the starting sample. Such methods may increase the dynamic range of dPCR and provides alternative analysis methods.

Figure 2:
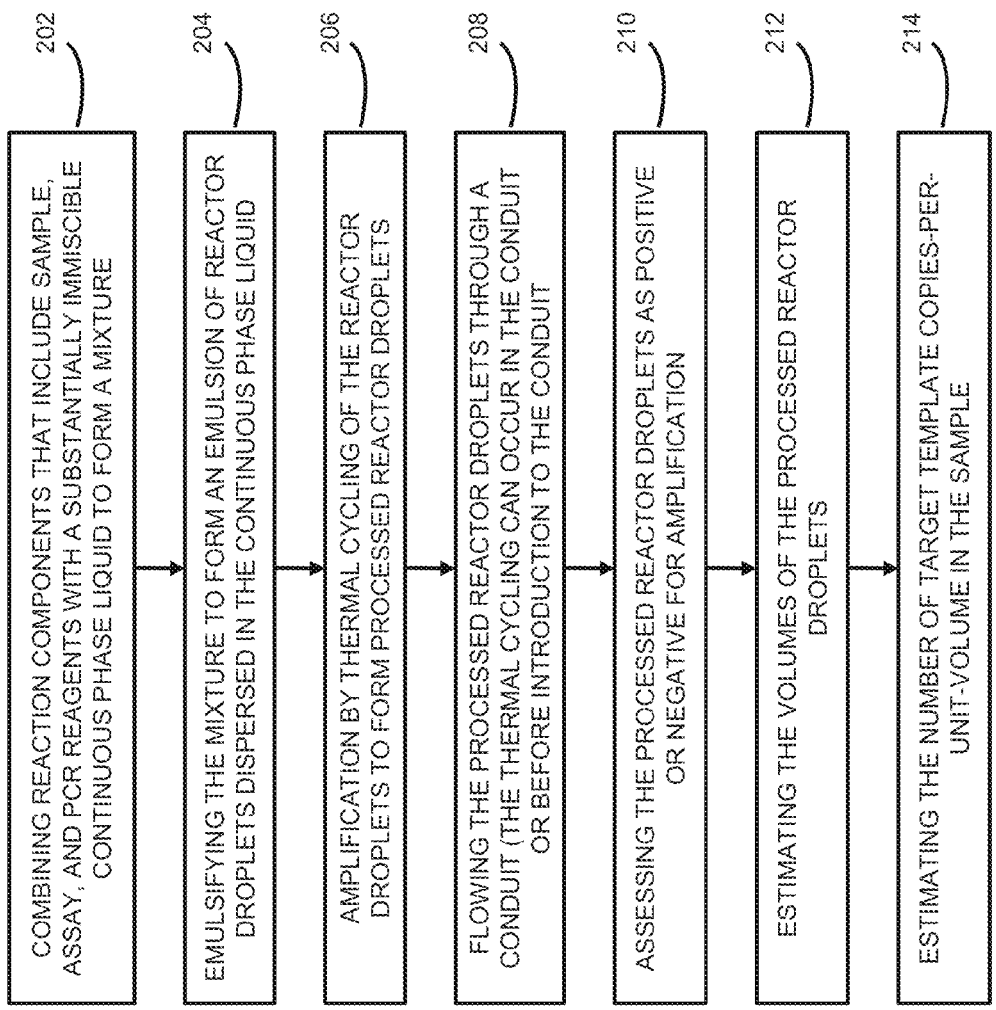
FIG. 2 is a flow diagram of another exemplary method according to various embodiments of the present teachings.

One exemplary method of this type is depicted in the flow chart shown in FIG. 2. As shown in FIG. 2, the method may first comprise generating a plurality of discrete sample portions. More particularly, generating the plurality of discrete sample portions includes combining reaction components that include sample, assay, and PCR reagents, with a substantially immiscible continuous phase liquid, to form a mixture. The mixture is emulsified to form the plurality of discrete sample portions. In various embodiments, the plurality of discrete sample portions is an emulsion of reactor droplets dispersed in the continuous phase liquid.

Amplification of the plurality of discrete sample portions may be accomplished by thermal cycling to form a plurality of discrete processed sample portions. The plurality of discrete sample portions may be flowed through a conduit before amplification. In other embodiments, the plurality of discrete processed sample portions, after amplification, may be flowed the conduit. The plurality of discrete processed sample portions are assessed to determine if the discrete sample portions are positive or negative for amplification. The volumes of the processed sample portions are estimated. Then, the number of target template copies-per-unit-volume in the sample may be estimated.

Figure 3:
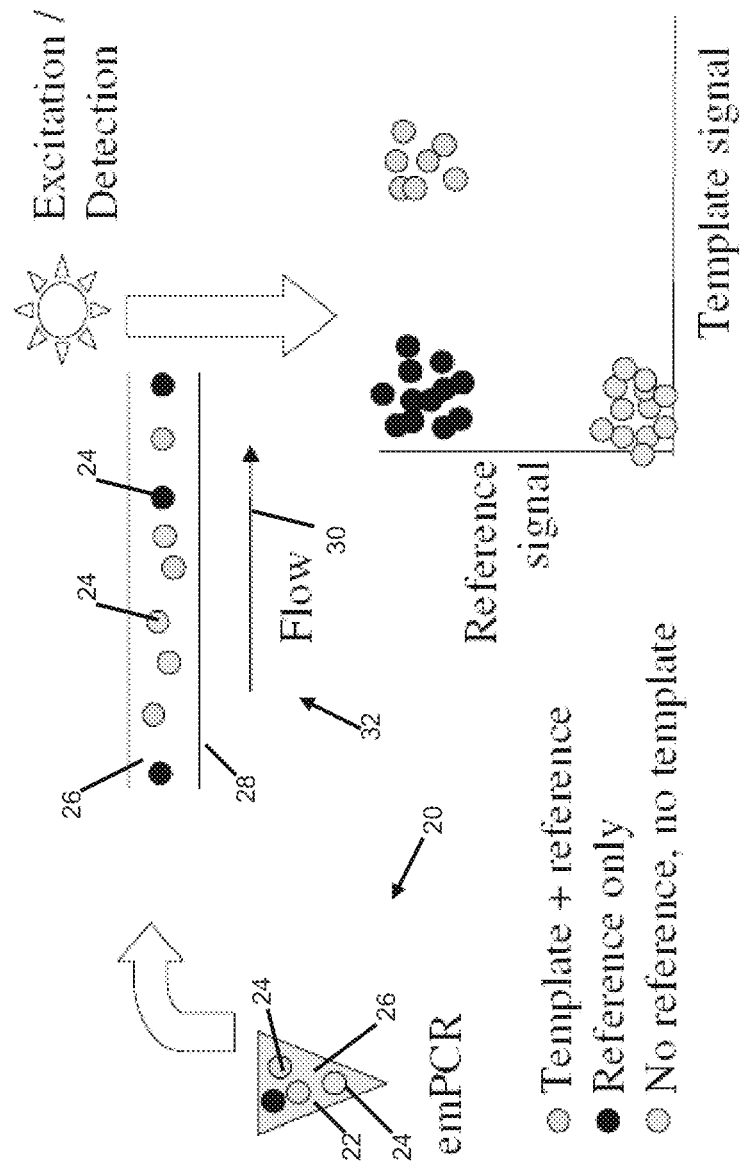
FIG. 3 is a schematic diagram of an exemplary system and method according to various embodiments of the present teachings.
Figure 4:
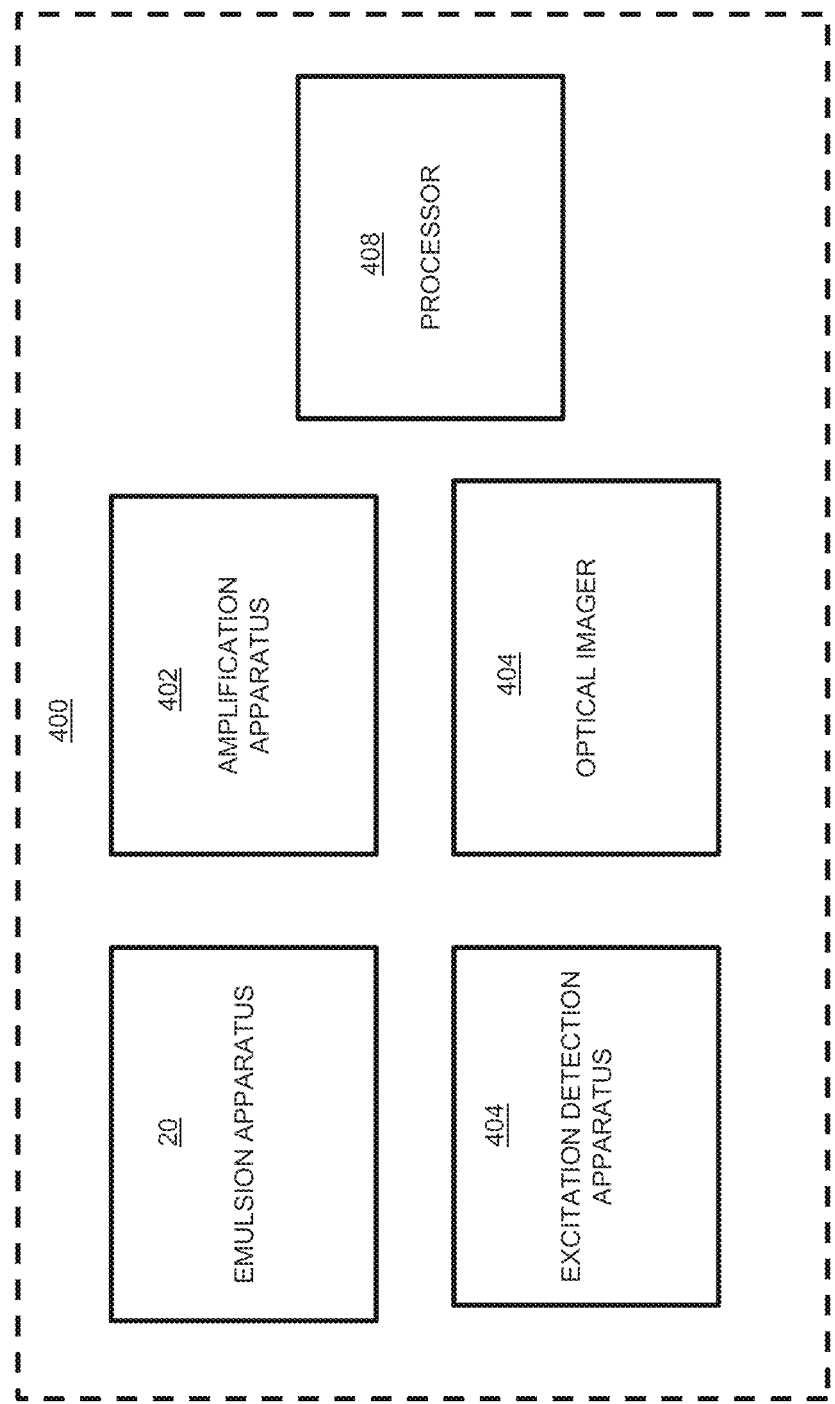
FIG. 4 is a block diagram of an exemplary system according to various embodiments of the present teachings.

FIG. 3 is a schematic diagram of an exemplary system and method according to various embodiments of the present teachings. In a first step of the method, an emulsion apparatus 20 is provided where an emulsion 22 is prepared comprising a plurality of discrete sample portions 24. With reference to FIG. 4, an exemplary dPCR system 400 is illustrated, including emulsion apparatus 20 for forming a plurality of discrete sample portions. In some embodiments, the discrete sample portions 24 may be droplets of an aqueous sample dispersed in a substantially immiscible carrier 26, for example, in a fluorinated liquid.

Figure 5B:
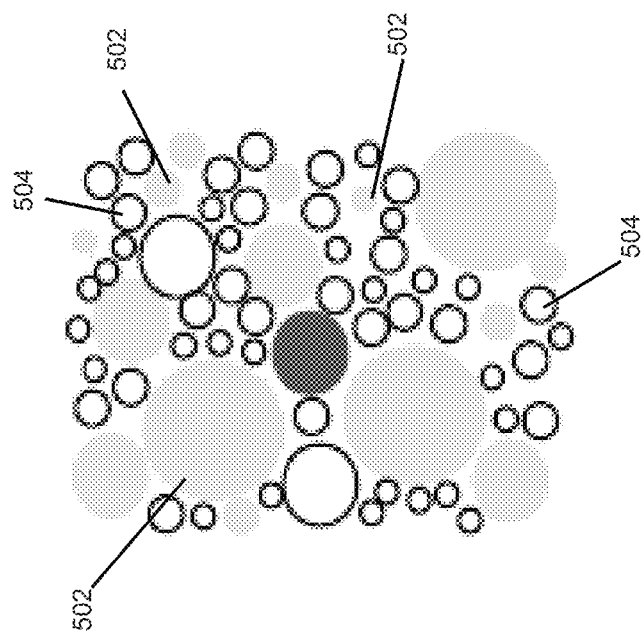
FIG. 5B depicts a plurality of discrete processed sample portions according to various embodiments of the present teachings.
Figure 5A:
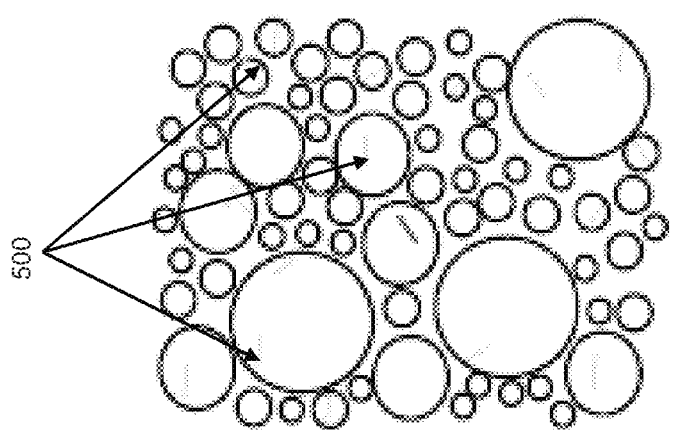
FIG. 5A depicts a plurality of discrete sample portions according to various embodiments of the present teachings.

FIG. 5A illustrates target nucleic acids 500 contained within discrete sample portions of various sizes. Emulsion 22 is then amplified. In some embodiments, the amplification is accomplished by an amplification apparatus 402, referring back to FIG. 4, thermally cycling such that the discrete sample portions containing a target nucleic acid are replicated within the discrete sample portion. The amplification apparatus may be a PCR instrument. In another example, the amplification apparatus may be a serpentine thermal cycler. In some embodiments, after amplifying, emulsion 22 is then moved into and through a conduit 28 in the direction of flow shown by flow arrow 30, in a flow cytometry station 32. In conduit 28, the discrete sample portions 24 may be separated, for example, to form a single-file line of sample portions. Within, at an exit of, or adjacent an exit of, conduit 28, an excitation detection apparatus 34 can be located where each discrete sample portion is illuminated by an excitation source 36 and fluorescence that may result from the illumination may be detected, indicating positive amplification of the target nucleic acid.

FIG. 5B illustrates discrete sample portions with positive amplification 502 as well as discrete sample portions with negative amplification 504. The plurality of discrete sample portions may contain a reference dye only, contain no reference dye and no target nucleic acid, or contain a reference dye and a target nucleic acid.

Following excitation and detection by an excitation detection apparatus 404, with reference again back to FIG. 4, a plot of the results can be generated as shown graphing the detected target nucleic acid signal against the detected reference signal. The excitation and detection apparatus 404 can comprise one or more of the excitation and detection components described, for example, in U.S. Patent Application Publication No. US 2007/0141593 A1 to Lee et al., which is incorporated herein in its entirety by reference.

In an exemplary embodiment, a TAQMAN® fluorescent probes qPCR reaction with target cDNA is overlayed with a 5-fold higher volume of mineral oil in a 96-well plate. An inverse emulsion may be created in an ultrasonic bath. The plurality of discrete sample portions formed using this method comprises sample portions from about 1 fL to about 1 pL in volume. The plurality of discrete sample portions may be thermally cycled in the plate until a plateau of replicates is produced in the positive discrete sample portions. With reference back to FIG. 4, an optical imager 404 may be used to image the plurality of discrete sample portions in order to determine size and volume of the discrete sample portions. For example, the discrete sample portions may be analyzed using an optical camera, or flow cytometry, to estimate the size (volume) and to determine positivity. Instead of estimating the copy number per droplet, however, the user determines the droplet volume that delivered a certain frequency of positivity. For example, one could ask what discrete sample portion size delivered positive amplification reactions at a 66% frequency. If 1 pL discrete sample portions delivered this frequency, then the initial target concentration would be $1.7 \times 10^{-12}$ M (1.7M). If 1 fL discrete sample portions delivered this frequency, then the initial target concentration would be $1.7 \times 10^{-9}$ (1.7 nM). In an alternative embodiment, the discrete sample portions positivity frequency may be plotted by discrete sample portions size. The slope of a portion of the resulting curve may be used to estimate the initial discrete sample portion concentration.

Furthermore, dPCR system 400 can include one or more processors, such as a processor 408. As such, generating any plots or determining the estimating the number of copies-per-unit-volume of the at least one target nucleic acid in the sample based on the number of discrete processed sample portions determined to contain the at least one target nucleic acid therein, according to embodiments of the present teachings, may be calculated by processor 408. Processor 408 can be implemented using a general or special purpose processing engine such as, for example, a microprocessor, controller or other control logic. Processor 408 may be included in a separate computing system, or in any one of optical imager 404, excitation detection apparatus 404, amplification apparatus 402, or emulsion apparatus 20.

It will be appreciated that, for clarity purposes, the above description has described embodiments of the invention with reference to different functional units and processors. However, it will be apparent that any suitable distribution of functionality between different functional units, processors or domains may be used without detracting from the invention. For example, functionality illustrated to be performed by separate processors or controllers may be performed by the same processor or controller. Hence, references to specific functional units are only to be seen as references to suitable means for providing the described functionality, rather than indicative of a strict logical or physical structure or organization.

Forming Discrete Sample Portions

According to various embodiments, the present teachings provide a system including an emulsion apparatus, and a method that uses the same. The emulsion apparatus generates a plurality of discrete sample portions. The emulsion apparatus may generate the plurality of discrete sample portions by various methods, such as shaking, stirring, sonicating, extruding, or shear electowetting, for example. In some embodiments, the emulsion apparatus may be a sonicator, a vortexer, or a plate shaker. Emulsification parameters, such as emulsification method, strength/power, time, oil/surfactant chemistry, viscosity, concentration, aqueous phase composition, and water-to-oil ratio, for example, may be optimized to produce desired sizes for the discrete sample portions. In some embodiments, the discrete sample portions have a diameter of between 10 to 150 μm and a volume of between 1 pL to 1 nL.

Exemplary systems for methods of preparing and processing emulsions that may be used according to the present teachings include those described in U.S. patent application Ser. No. 12/756,547, filed Apr. 8, 2010, to Lau et al. for "System and method for preparing and using bulk emulsion," which is incorporated herein in its entirety by reference. Exemplary systems for methods of processing and thermally cycling emulsions that may be used according to the present teachings include those described in U.S. patent application Ser. No. 12/756,783, filed Apr. 8, 2010, to Liu et al. for "System comprising dual-sided thermal cycler and emulsion PCR in a pouch," which is also incorporated herein in its entirety by reference.

The method may further comprise diluting the sample to form a diluted sample and forming the plurality of discrete sample portions from the diluted sample. Dilution may comprise terminally diluting the sample to achieve an average of less than one of the at least one target nucleic acid molecules per sample portion. In some embodiments, the method further comprises: serially diluting different portions of the sample by different respective dilution ratios; dividing each serially diluted portion into a plurality of aliquots; and processing each of the plurality of aliquots of each of the serially diluted portions.

According to various embodiments, the components of the plurality of discrete sample portions may be provided in a multi-well plate. Forming the plurality of discrete sample portions may include emulsifying an aqueous sample with a medium that is at least substantially immiscible with the sample. In some embodiments, the emulsifying may comprise mixing the aqueous sample with the medium that is at least substantially immiscible with the sample in the multi-well plate, sonicating the aqueous sample with the medium that is at least substantially immiscible with the sample in the multi-well plate, shaking the aqueous sample in the medium that is at least substantially immiscible with the sample in the multi-well plate, or stirring the aqueous sample in the medium that is at least substantially immiscible with the sample in the multi-well plate. Emulsification to form a plurality of discrete sample portions may also take place in the presence of a surfactant, so that the kinetic stability of the emulsion increases. Some surfactants which may be used, but are not limited to, are Span80, STF9, ABIL EM90, and DC BY11-030, for example.

In various embodiments, polydisperse emulsions may be generated. Generally, polydisperse emulsions are less difficult to make, minimally handled, can be formed in batches, and greatly increase the dynamic range of dPCR. Furthermore, a small reaction chambers allow analysis without sample dilution that can introduce error. For example, heat, shaking, sonic energy, ultrasonic baths, combinations thereof, and the like can be used to produce emulsions, for example, to process batches of emulsions in 96-well, 384-well plates, or cell culture plates without the need for any special consumables to physically touch the samples. In other embodiments, a plate may be used based on the amplification apparatus. This greatly reduces the chance of cross-contamination. In addition, polydisperse emulsions typically vary in volume from about 1 fL to 10 pL, eliminating the need to dilute samples to achieve terminal dilutions. Since forming an emulsion may result in very small discrete sample portions, the method may further include removing very small droplets that may be problematic to detection or amplification.

In another embodiment, multi-mono dispersed emulsions may be formed. A multi-mono dispersed emulsion may include two or more sizes of discrete sample portions, where the sizes are known or predetermined. For example, a multi-mono dispersed emulsion may contain three different sizes of discrete sample portions that are substantially the same size as three different predetermined sizes. Substantially means within +/−10% of the predetermined size. By determining the plurality of discrete sample portions which size of the different predetermined sizes each discrete sample portion is, the volume of each discrete sample portion can be determined. Multi-mono dispersed emulsions may vary in volume from about 1 fL to 10 pL. In other words, each droplet can be binned into a predetermined size. In this way, the dynamic range can be increased and an optical imager may be simplified.

Any of a variety of substantially or totally immiscible fluids can be used as the carrier fluid. By immiscible what is meant is immiscible with respect to the aqueous sample droplets. The substantially or totally immiscible fluid can comprise, for example, paraffin oil, mineral oil, silicone oil, a perfluorinated polyether (PFPE), other fluorinated fluids, fluorinated solvents, combinations thereof, and the like. Some specific fluids that can be used as a carrier fluids include GALDEN® HT170 available from Solvay Solexis of West Deptford, N.J., other GALDEN® HT liquids available from Solvay Solexis, FC-40 available from 3M Company of St. Paul, Minn., and other FLUORINERT™ liquids available from 3M Company of St. Paul, Minn.

In some embodiments, forming the plurality of discrete sample portions may include diluting a sample to near the single molecule limit, and combining or mixed the sample with all reagents needed for a PCR. A good input quantity of template may comprise the dilution limit where each aqueous reactor volume contains 1 or 0 target nucleic acid molecules, for example, such that the Poisson parameter, $\lambda$, is close to or equal to 1. If desired, in order to determine an optimal dilution, an initial quantification using, for example, a QUBIT® system (available from the Qubit Systems Inc., Kingston, Ontario, Canada) may be used. Unlike lower-replicate dPCR embodiments, the system and method of the present teachings can accommodate a much larger deviation from an ideal $\lambda=1$ input concentration.

Emulsification and Sampling

In various embodiments, a method to prevent evaporation of the aqueous droplets in water-in-fluorocarbon emulsions is provided. In this way, errors in sampling an emulsion of a plurality of discrete sample portions are minimized. Discrete sample portions, in this case aqueous droplets, are formed by adding hydrocarbon oil into a water-fluorocarbon mixture and agitating the three phases together. As such, after emulsification the hydrocarbon oil forms a layer covering the aqueous droplets to prevent evaporation.

Density of aqueous phase is around 1 g/cc. Density of fluorocarbon (FC) fluid is about 1.6-1.8 g/cc. Thus, in water-in-fluorocarbon emulsions, aqueous droplets form a layer on top of FC fluid due to the density difference. Without a layer to cover the aqueous droplets, the aqueous droplets may evaporate during storage. Furthermore, evaporation becomes more severe if the emulsion is heated, for example, in the thermal cycles of the PCR process. Droplets may shrink or evaporate completely, inhibiting biological reactions inside the droplets and making post-amplification droplet sizing difficult.

According to various embodiments, hydrocarbon oil may be layered on top of the layer of aqueous droplets. The density of hydrocarbon oil is about 0.8 g/cc. Thus, the hydrocarbon oil is immiscible with both water and fluorocarbon. The hydrocarbon oil layer reduces evaporation of the aqueous droplets. However, if the hydrocarbon oil is added after emulsification, this extra step increases complexity of the process and time. Furthermore, if many parallel emulsion vessels (e.g. sealed PCR wells) need to be opened to add hydrocarbon oil, it may increase the chance of cross contamination among vessels.

According to various embodiments, hydrocarbon oil is added into the vessels together with a water-fluorocarbon fluid mixture before the emulsification or agitation. Thus there are three phases existing in the vessel. The FC phase contains the fluorocarbon fluid and a surfactant (fluorosurfactant) to make water-in-fluorocarbon emulsion. In one example, the fluorocarbon fluid is HFE7500 (3M), the fluorosurfactant is a block copolymer containing hydrophilic poly(ethylene glycol) (PEG) block and fluorophilic poly(perfluoropropylene ether) (PFPE) block, the hydrocarbon oil is a heavy mineral oil (Sigma-Aldrich 330760), and the aqueous phase includes sodium chloride (NaCl) solution 100 mM in distilled water. The aqueous phase contains water and biological reagents. The hydrocarbon (HC) phase contains only neat hydrocarbon oil, but no surfactant. The hydrocarbon oil is agitated together with water-fluorocarbon fluid mixture. After the agitation the aqueous phase is broken into small aqueous droplets stabilized by the fluorosurfactant and these aqueous droplets form a layer on top of the fluorocarbon fluid. The hydrocarbon oil forms a layer on top of the aqueous droplet layer preventing the evaporation of the aqueous droplets.

In one example, the vessel may be a MICROAMP® Optical 96-Well Reaction Plate (Applied Biosystems, 4316813) with MICROAMP® Clear Adhesive Film (Applied Biosystems, 4306311). Tube strips can also be used, e.g. Molecular BioProducts PCR 8-Tube Strips.

EXAMPLE 1

50 uL HFE7500 with 2 wt % fluorosurfactant, 10 uL NaCl and 40 uL heavy mineral oil were added in this order into each well on the plate. The plate was sealed by the adhesive film. When a tube strip is used, the tubes are sealed with cap strip.

The plate or the tube strip was then shaken by an oscillating mixer (RETSCH® MM301) with appropriate adapters. The operating parameter used in this example was 15 Hz for 1 min.

Figure 8B:
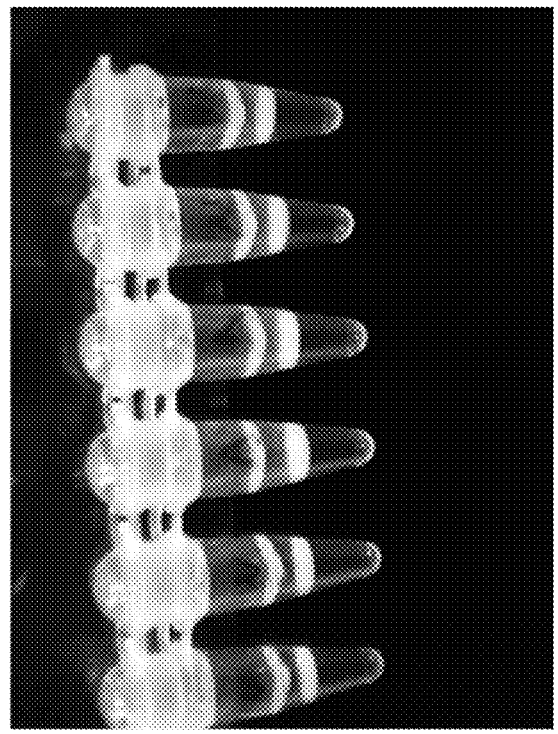
FIGS. 8A and 8B illustrate a three layered emulsion according to various embodiments of the present teachings.
Figure 8A:
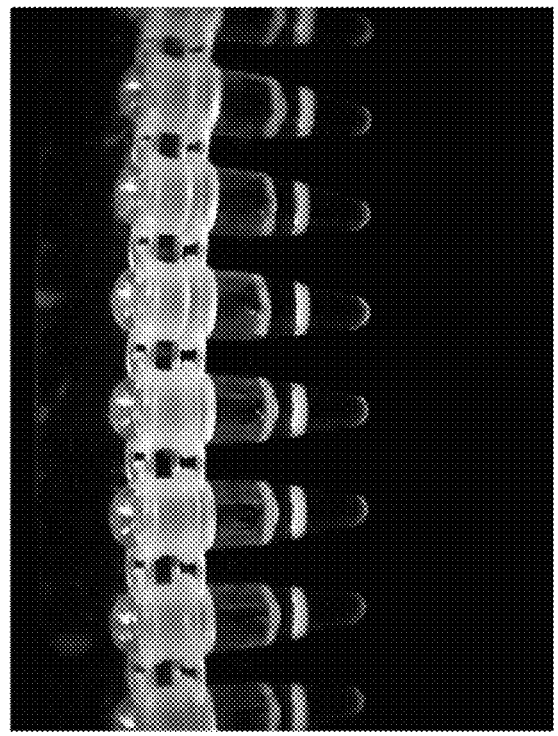

After shaking, the plate was unloaded from the mixer and kept in the upright position. A layer formed above the HFE7500. This layer contains the aqueous droplets stabilized by the fluorosurfactant. A clear mineral oil layer was formed on top the droplet layer, preventing the evaporation of aqueous droplets. This three-layered emulsion assembly in a tube-strip is depicted in FIG. 8A.

The plate or the tube strip with the emulsion sample was thermocycled between 95° C. and 60° C. for at least 40 cycles and no significant evaporation was observed. This three-layered assembly in a tube-strip after thermocycles is depicted in FIG. 8B.

Sampling

According to other embodiments, a method to sample the emulsion for subsequent analysis of the individual droplets is provided.

Figure 9:
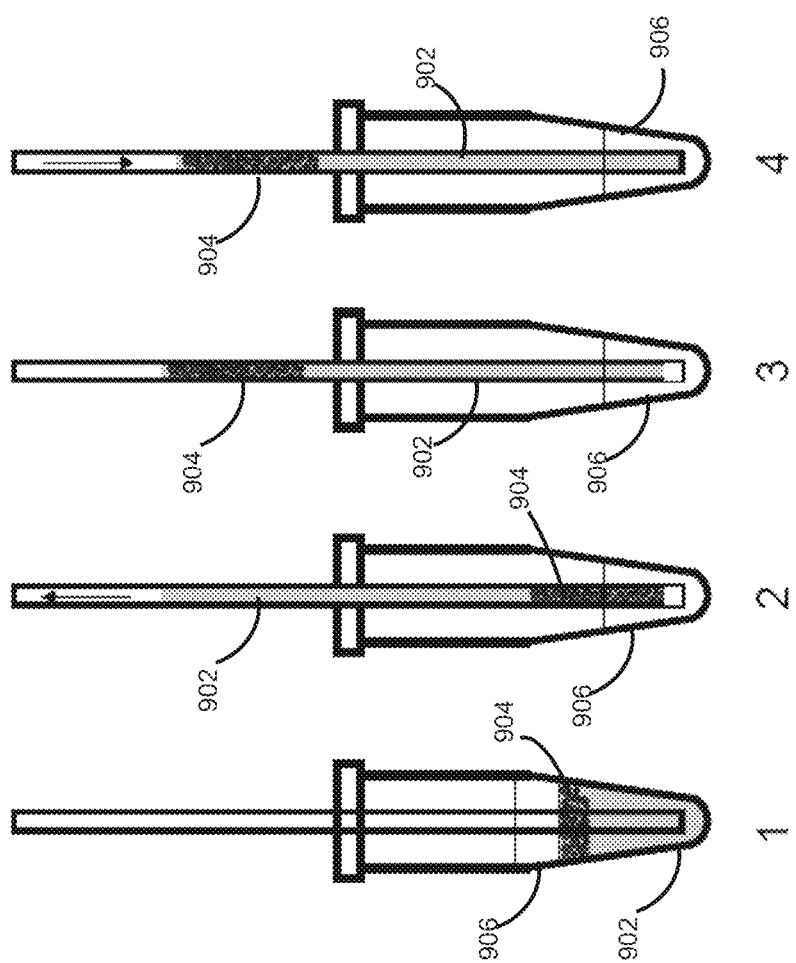
FIG. 9 illustrates a method of preparing a sample according to various embodiments of the present teachings.
Figure 10:
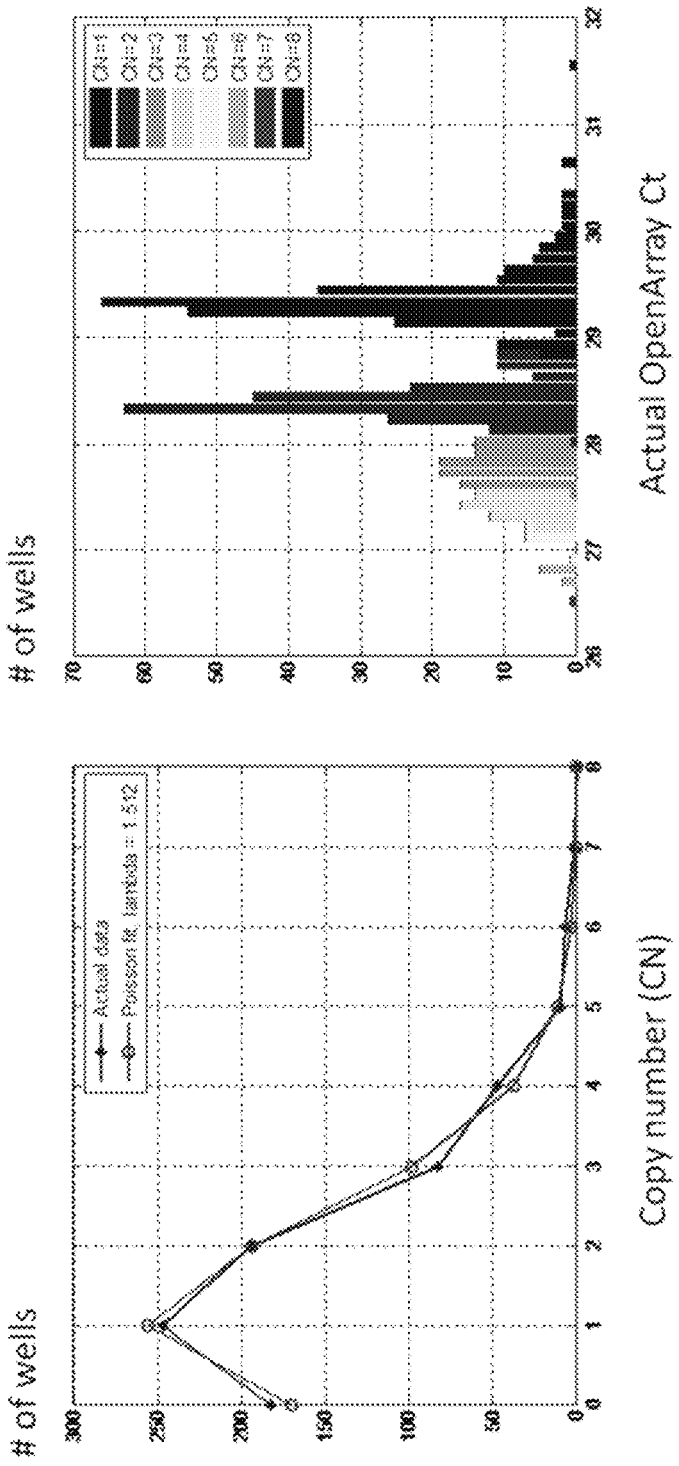
FIGS. 10-15 illustrate exemplary plots showing a relationship between $C_q$ and copy number according to various embodiments of the present teachings.
Figure 11:
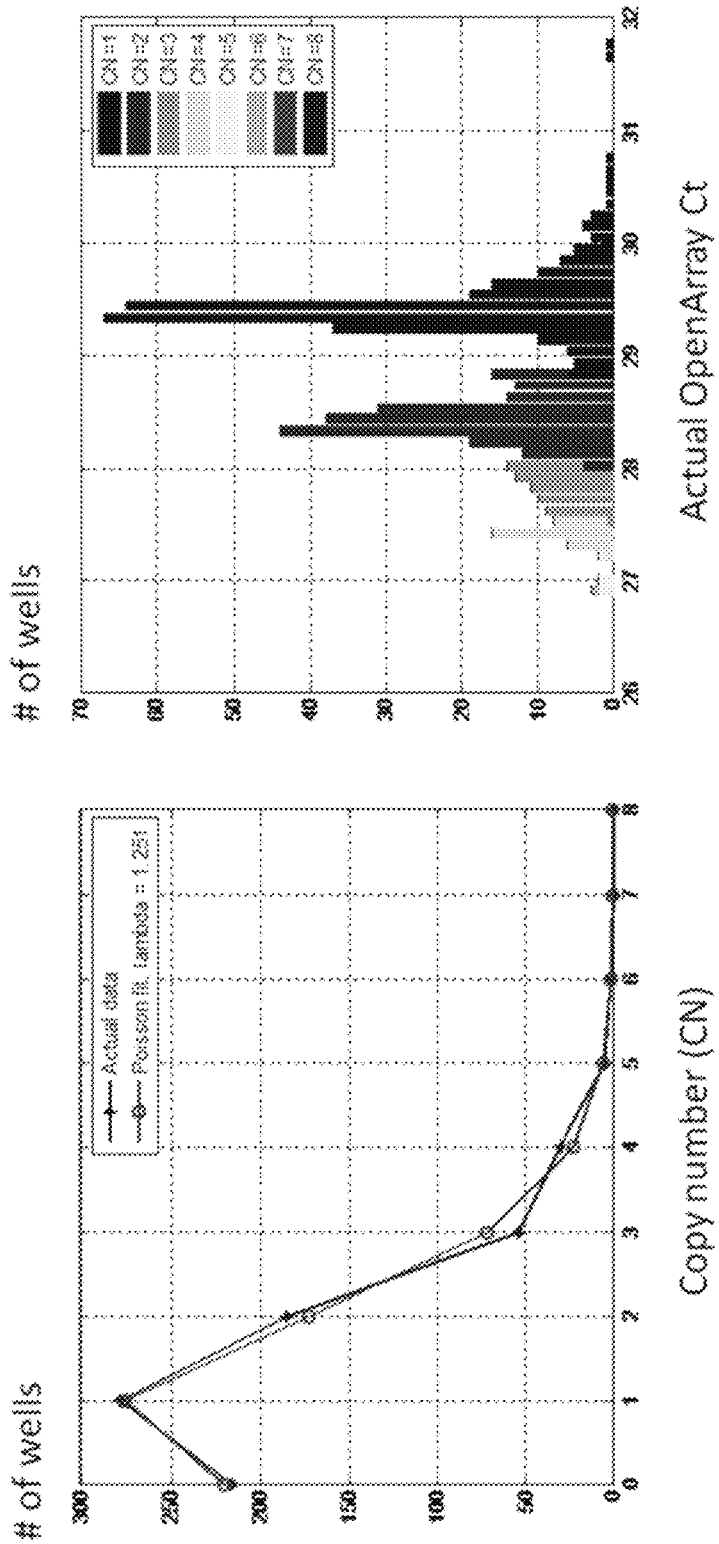
Figure 12:
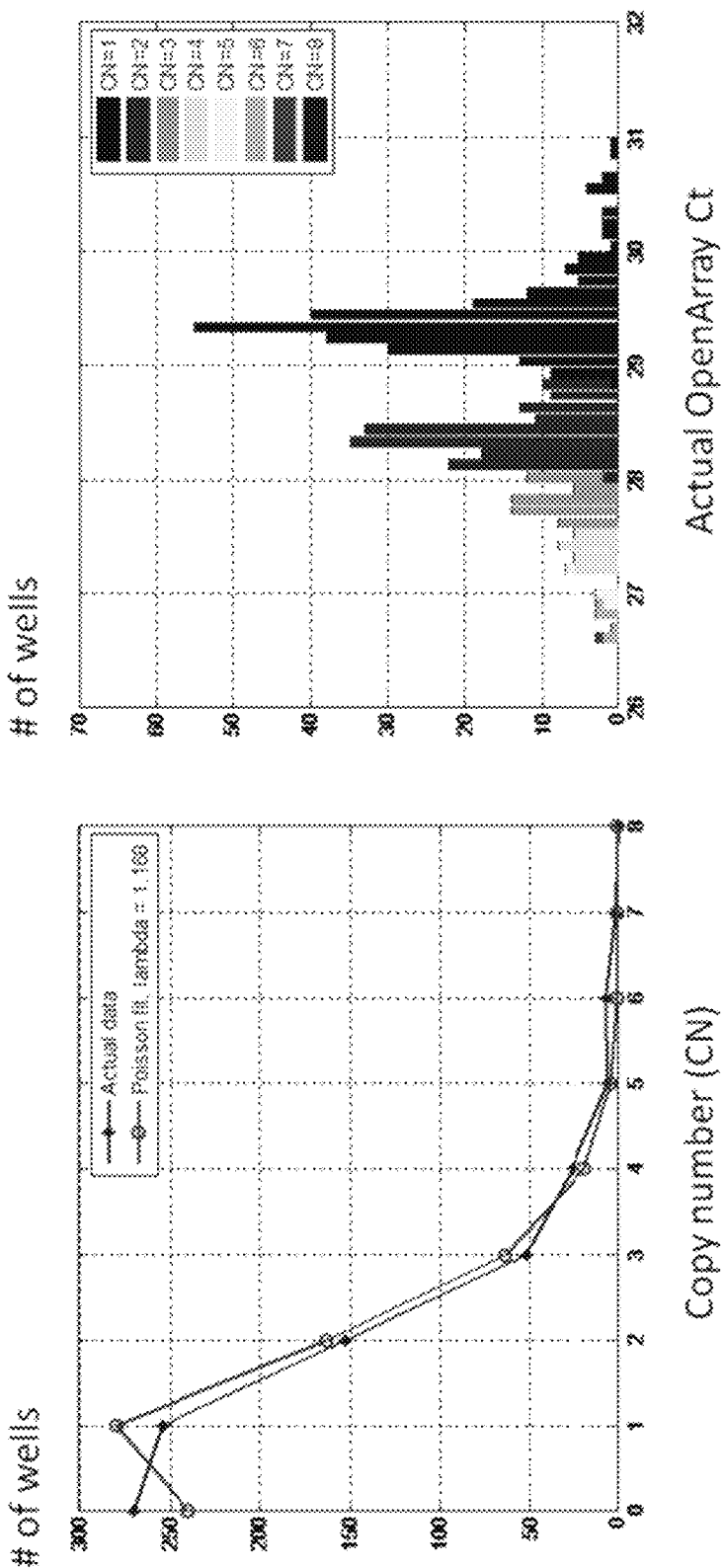
Figure 13:
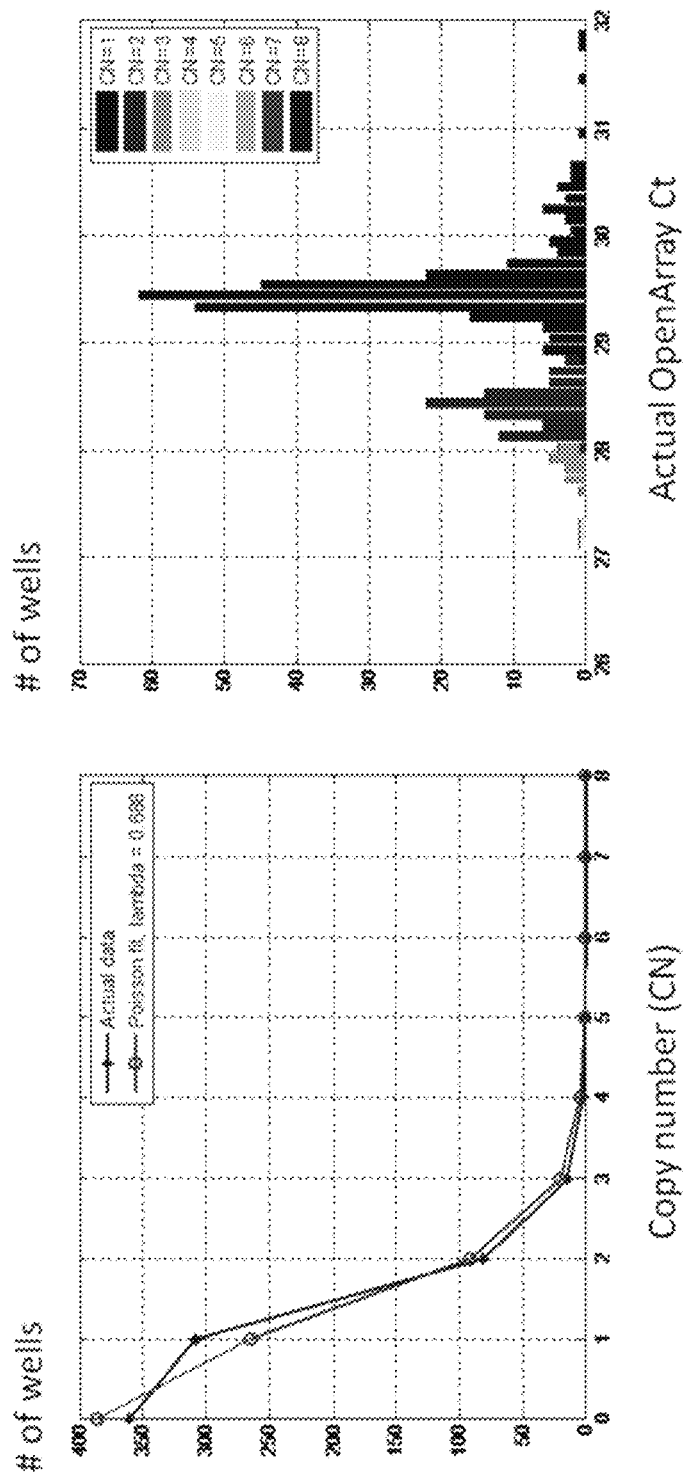
Figure 14:
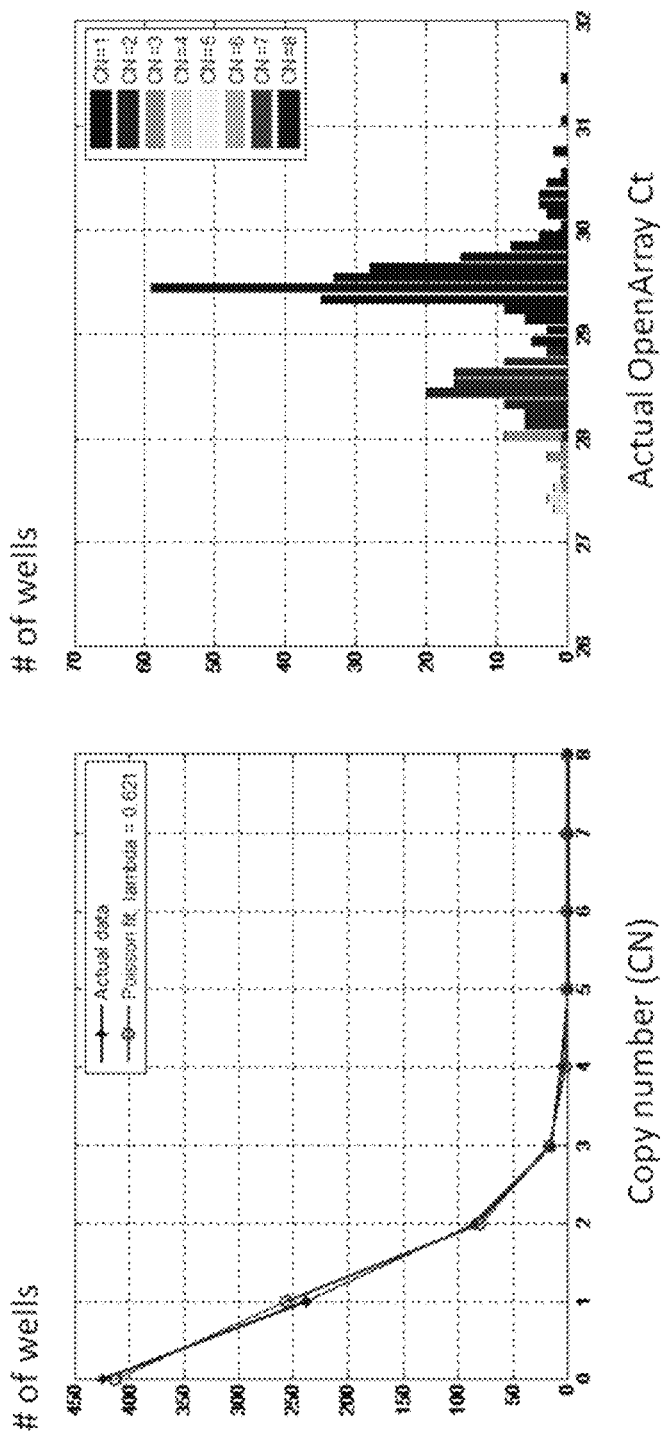
Figure 15:
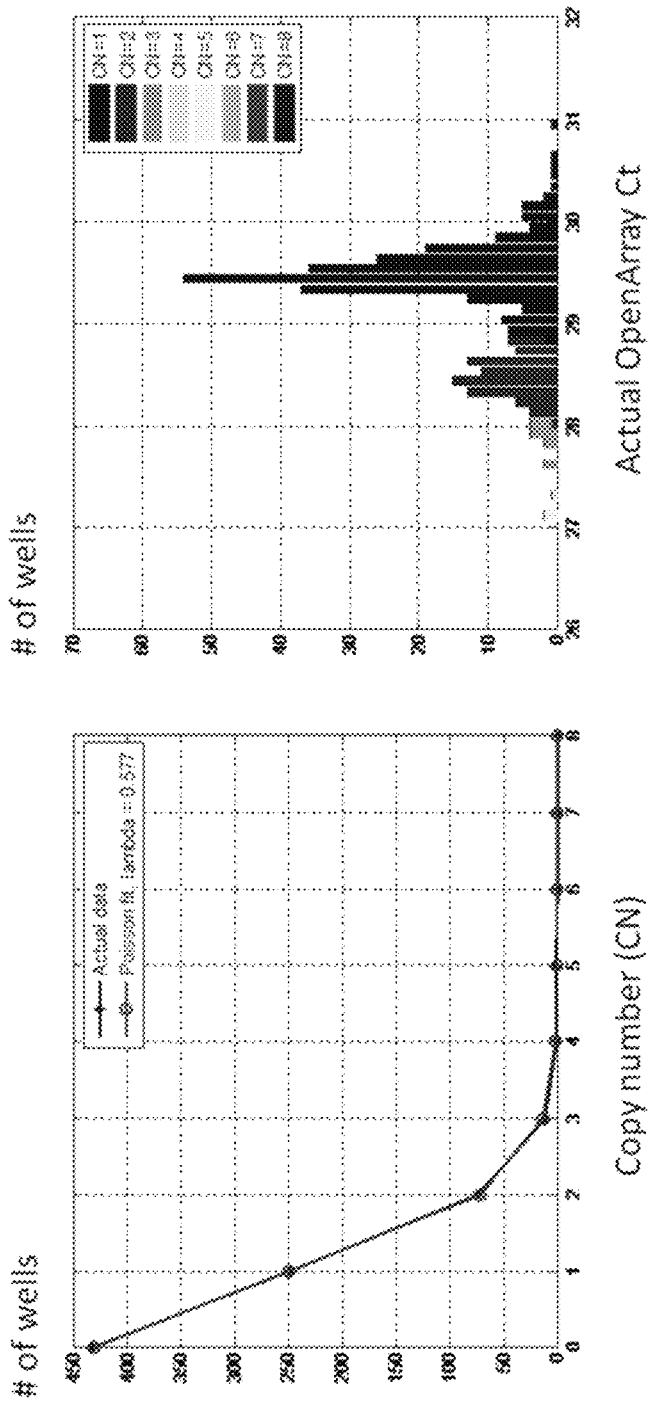
Figure 16:
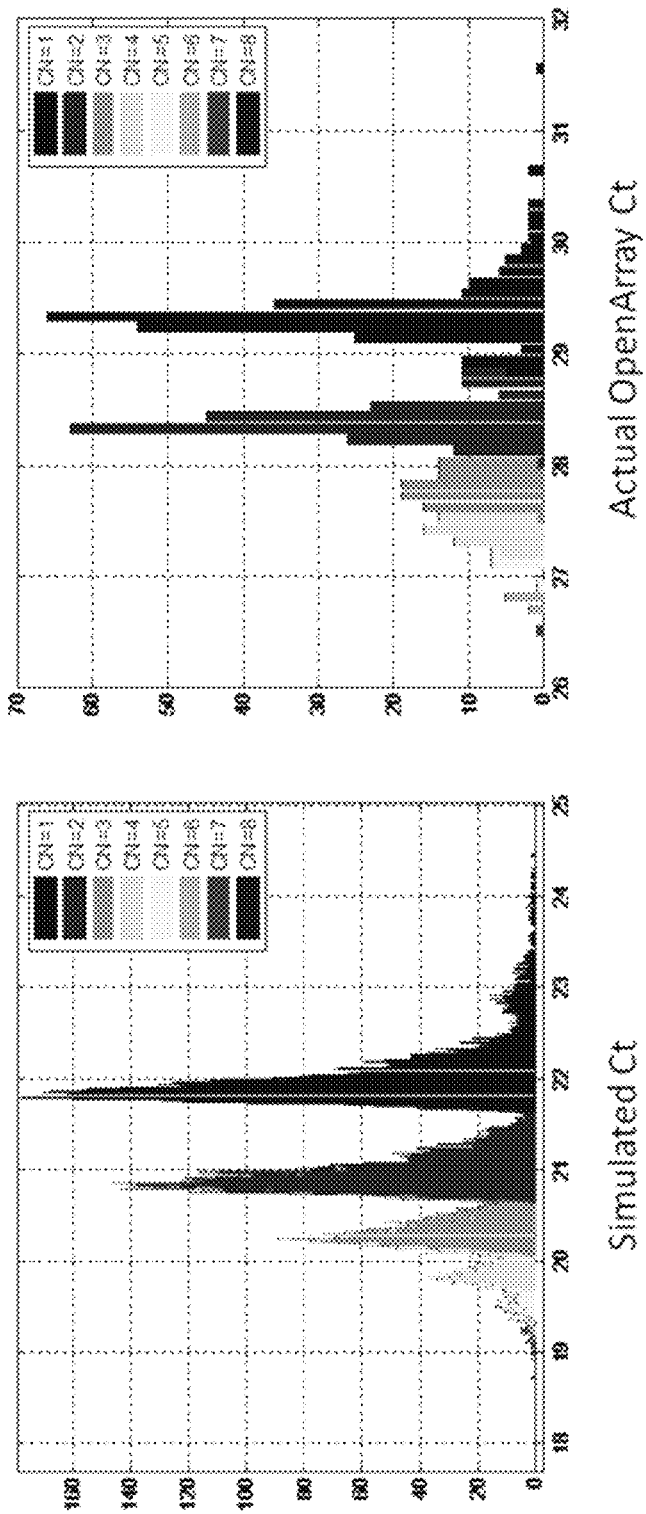
FIGS. 16-21 illustrate exemplary modeled $C_q$ plots versus actual $C_q$ plots.
Figure 17:
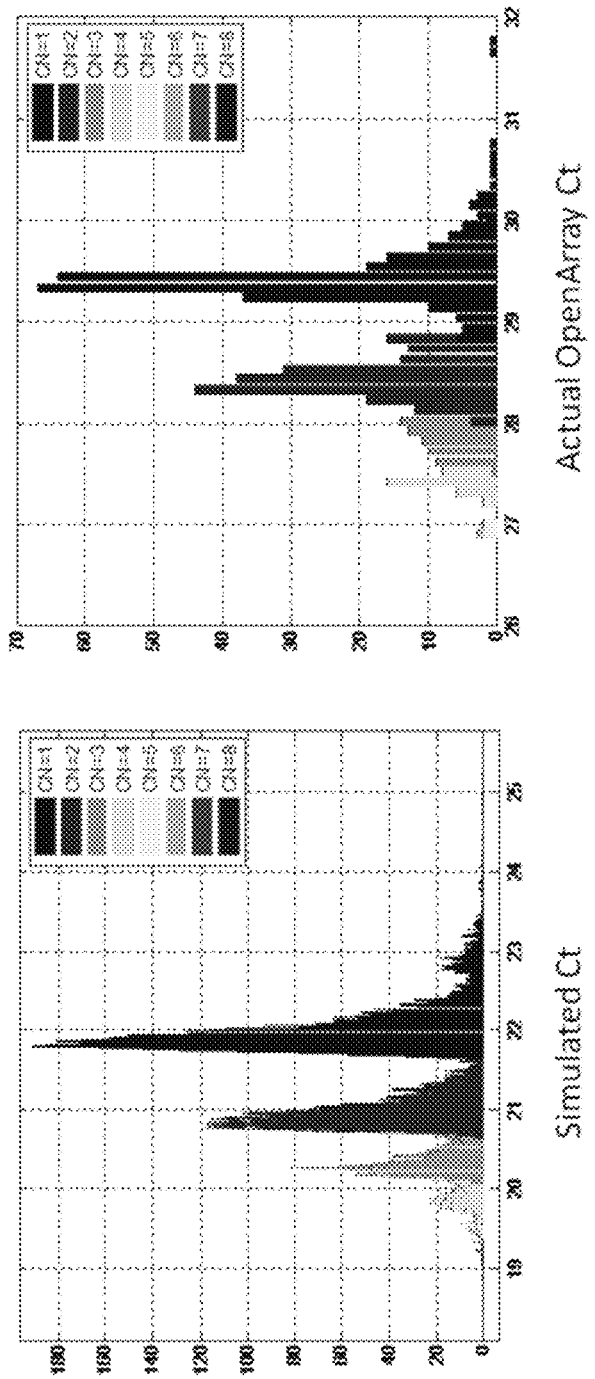
Figure 18:
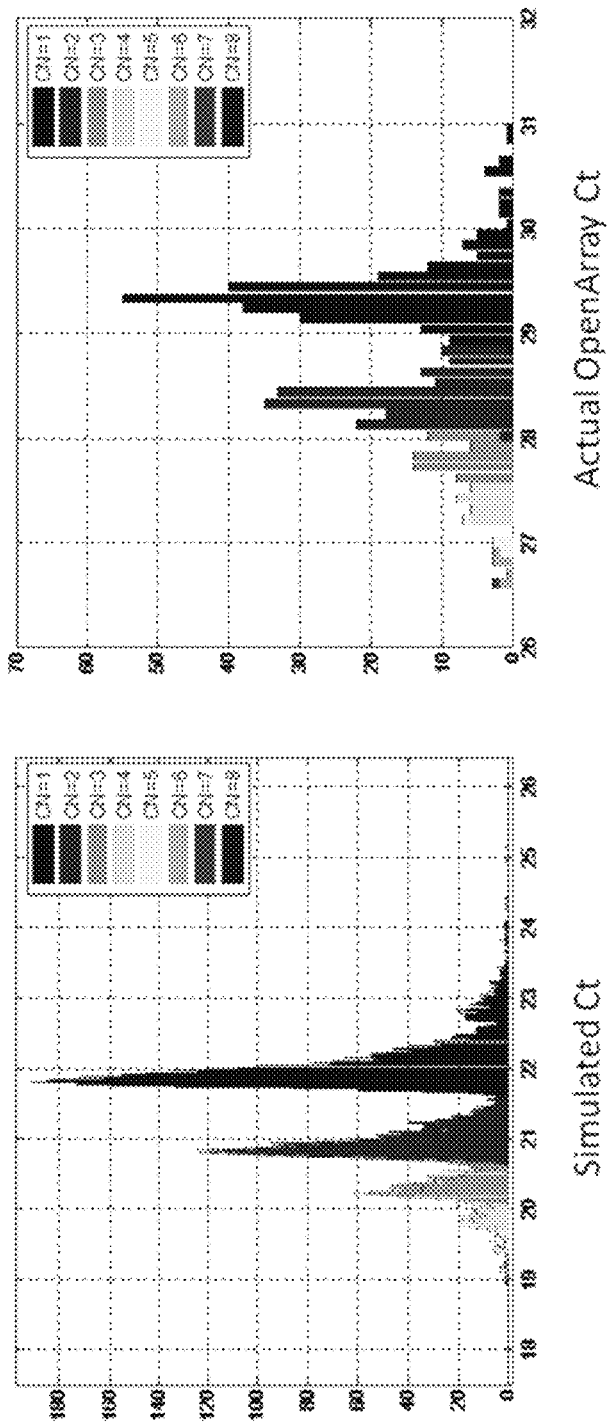
Figure 19:
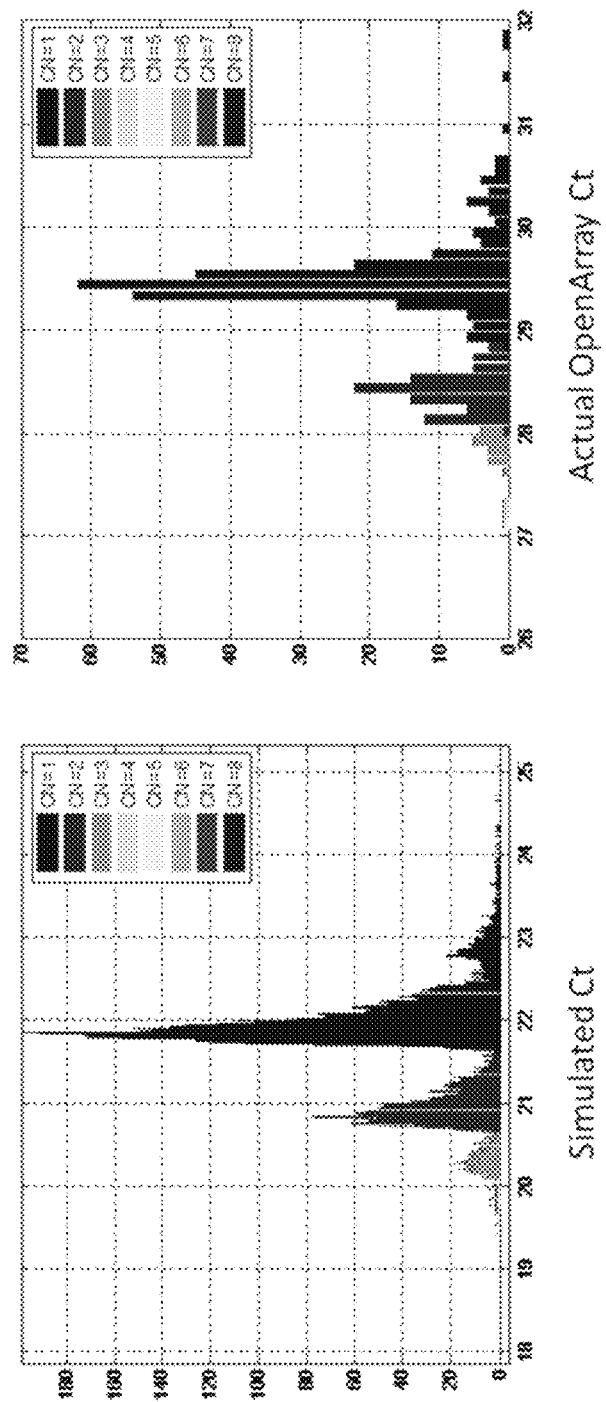
Figure 20:
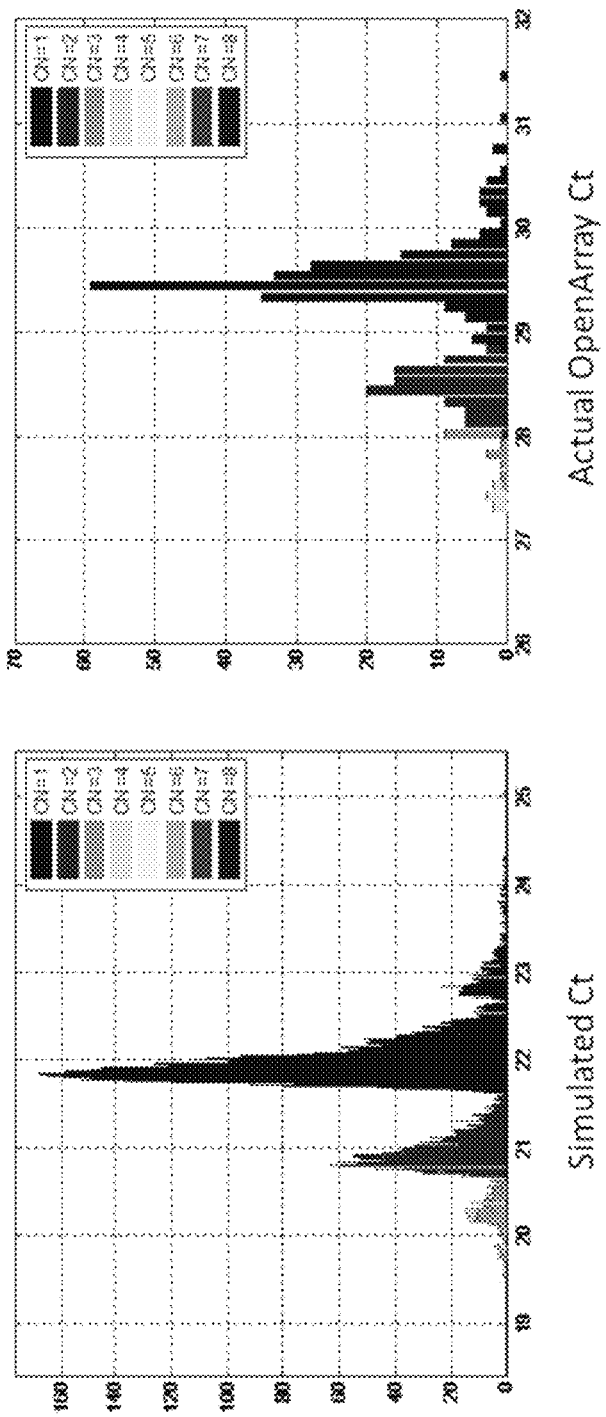
Figure 21:
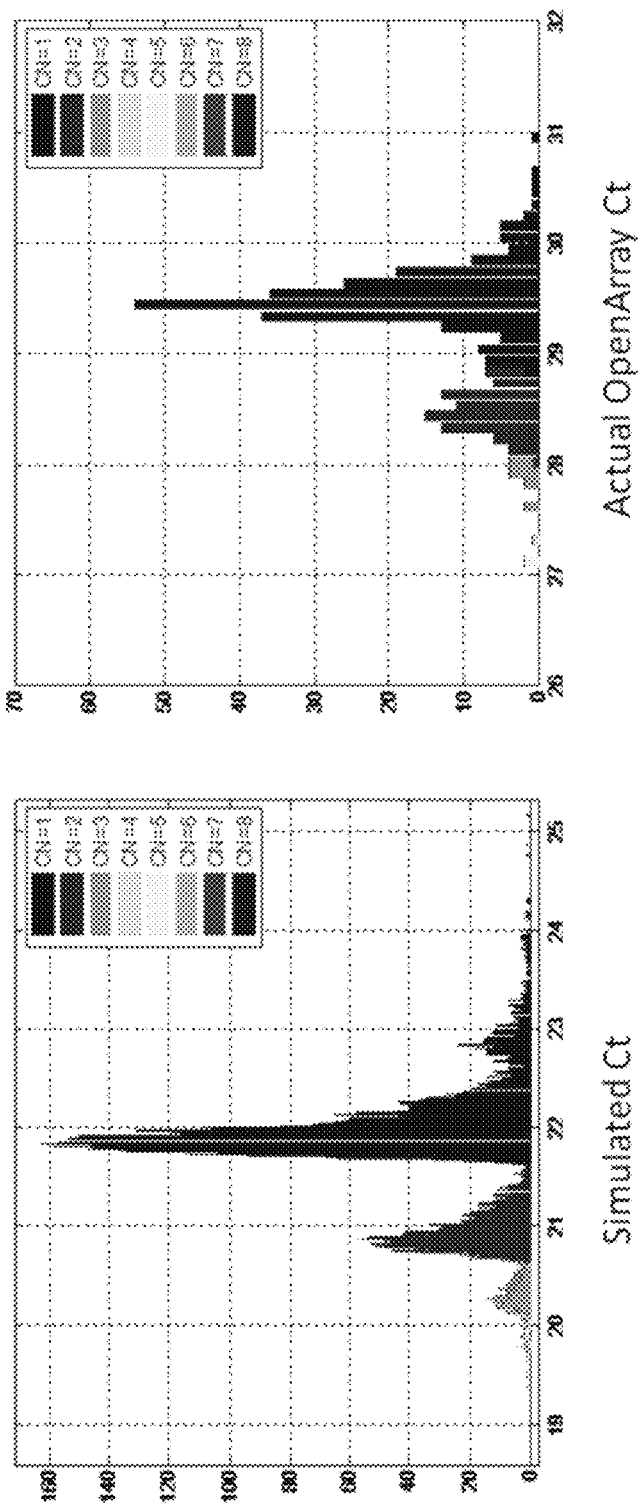
Figure 22:
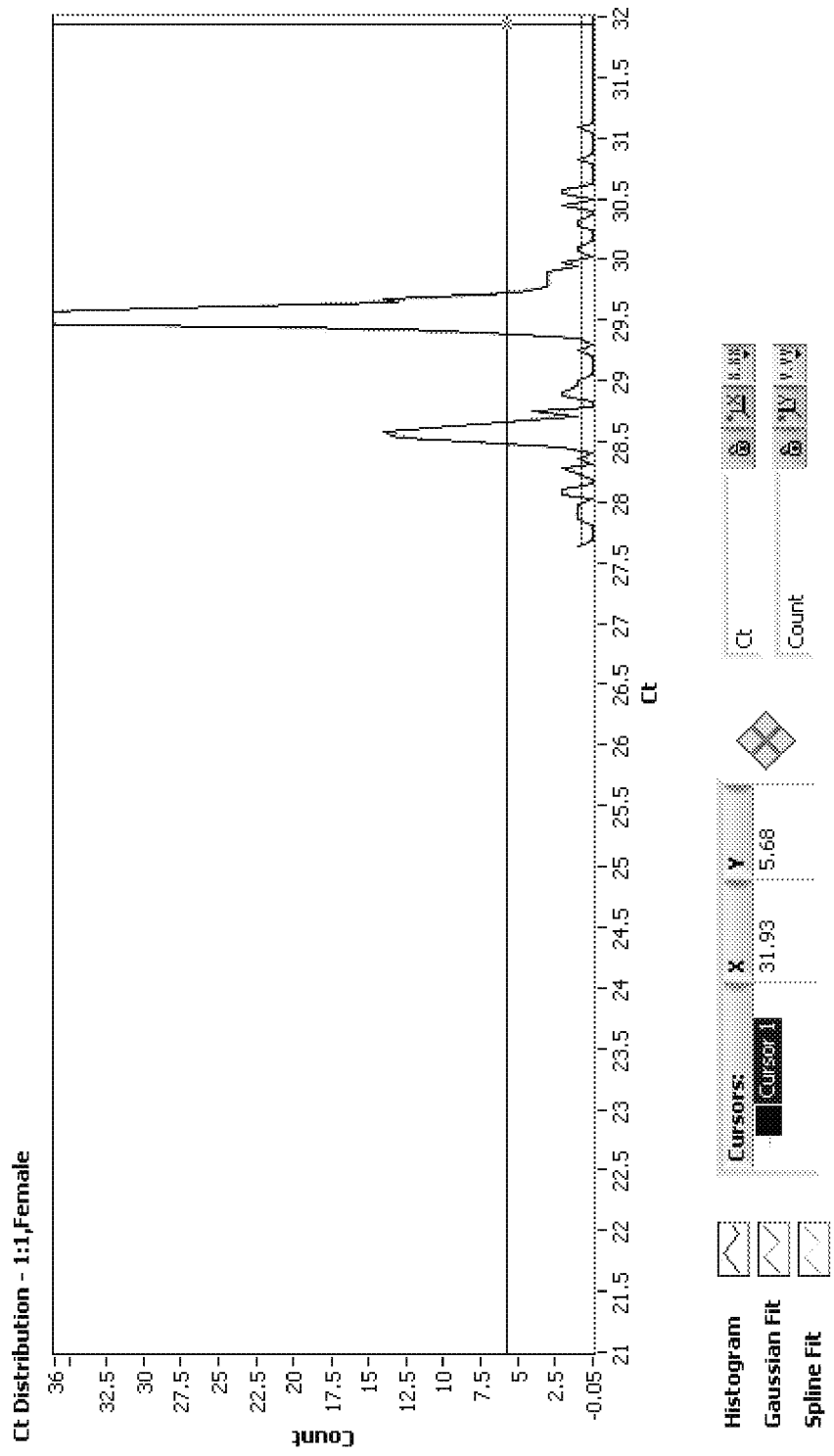
FIGS. 22-33 illustrate exemplary $C_q$ distributions according to various embodiments of the present teachings.
Figure 23:
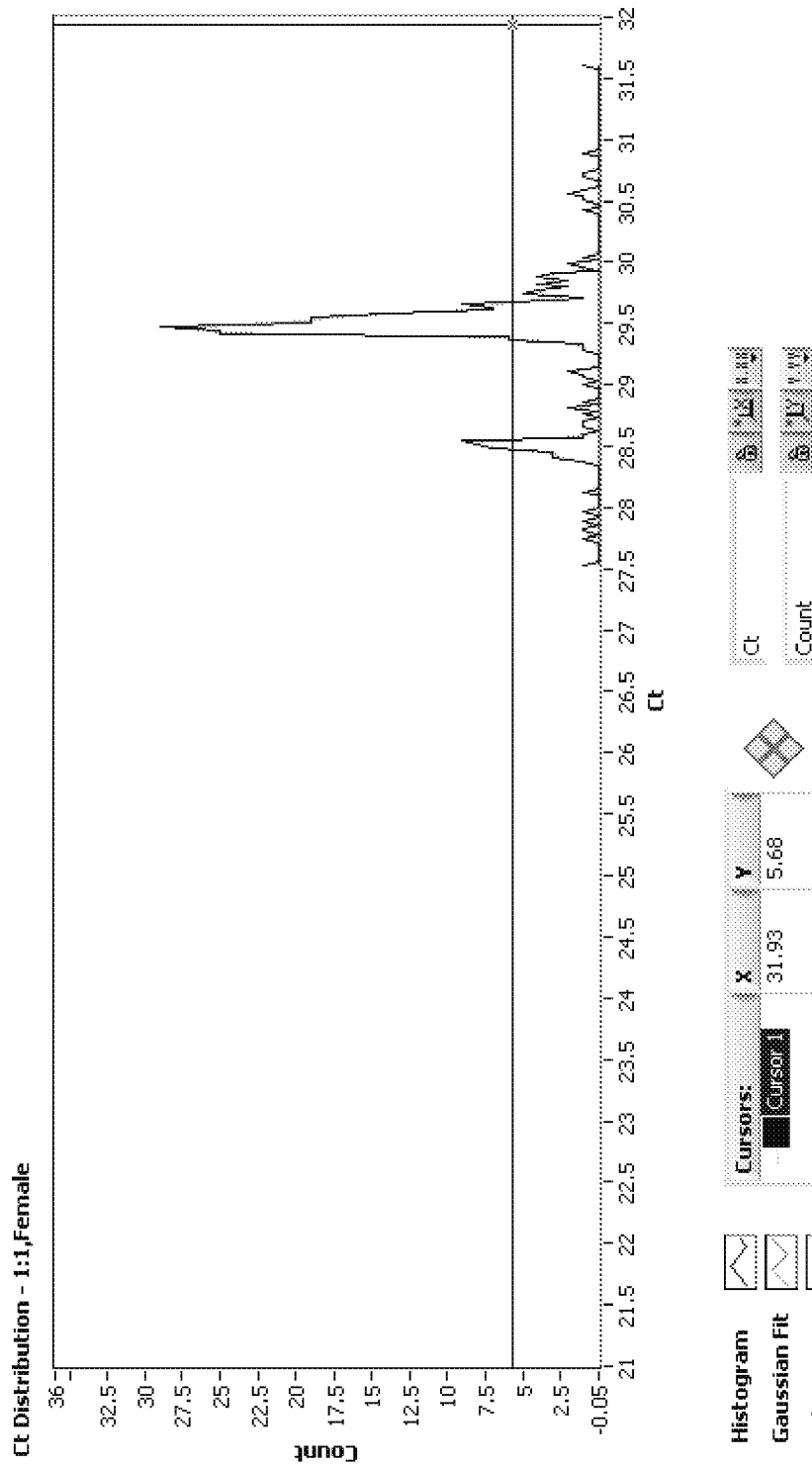
Figure 24:
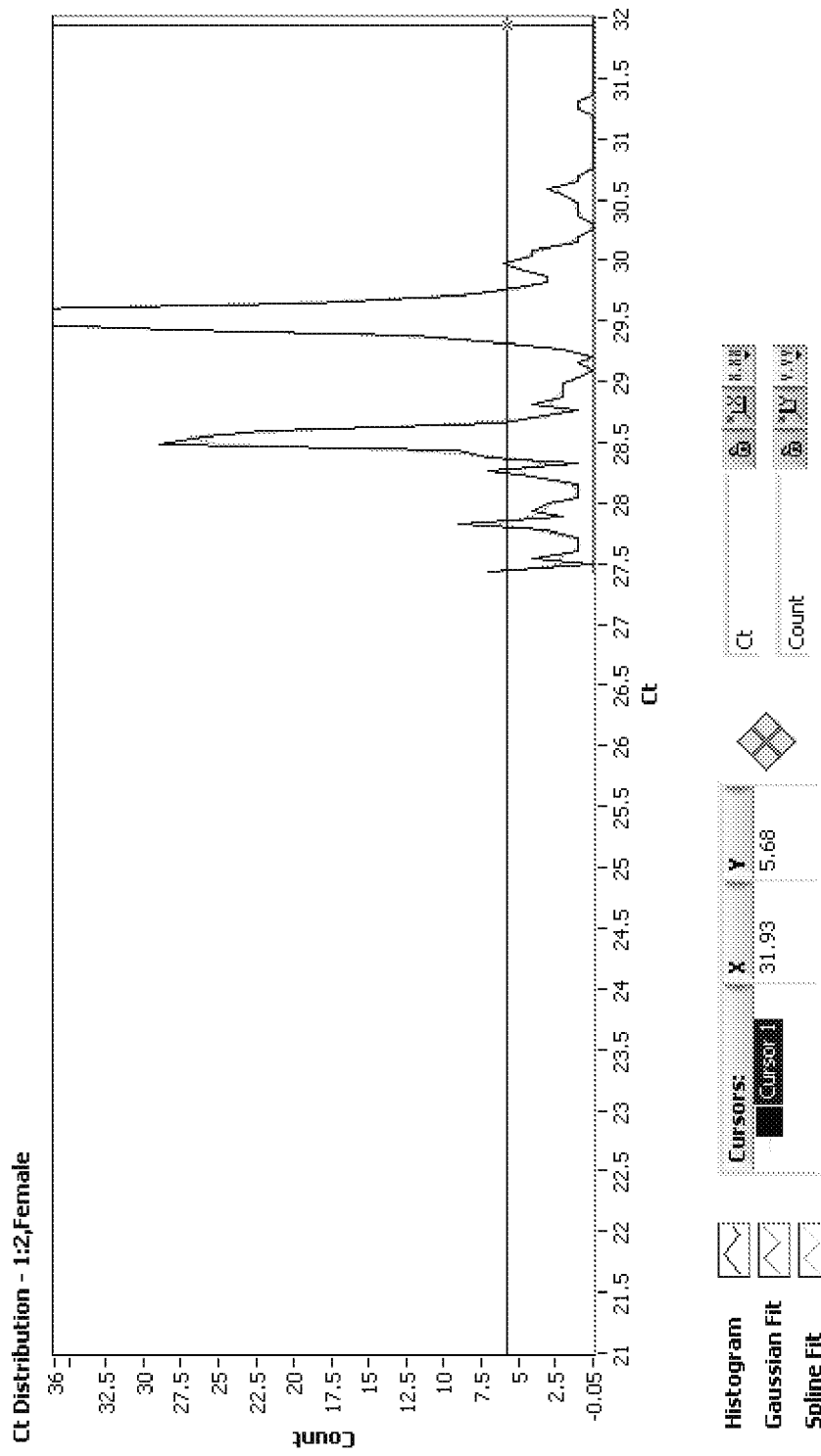
Figure 25:
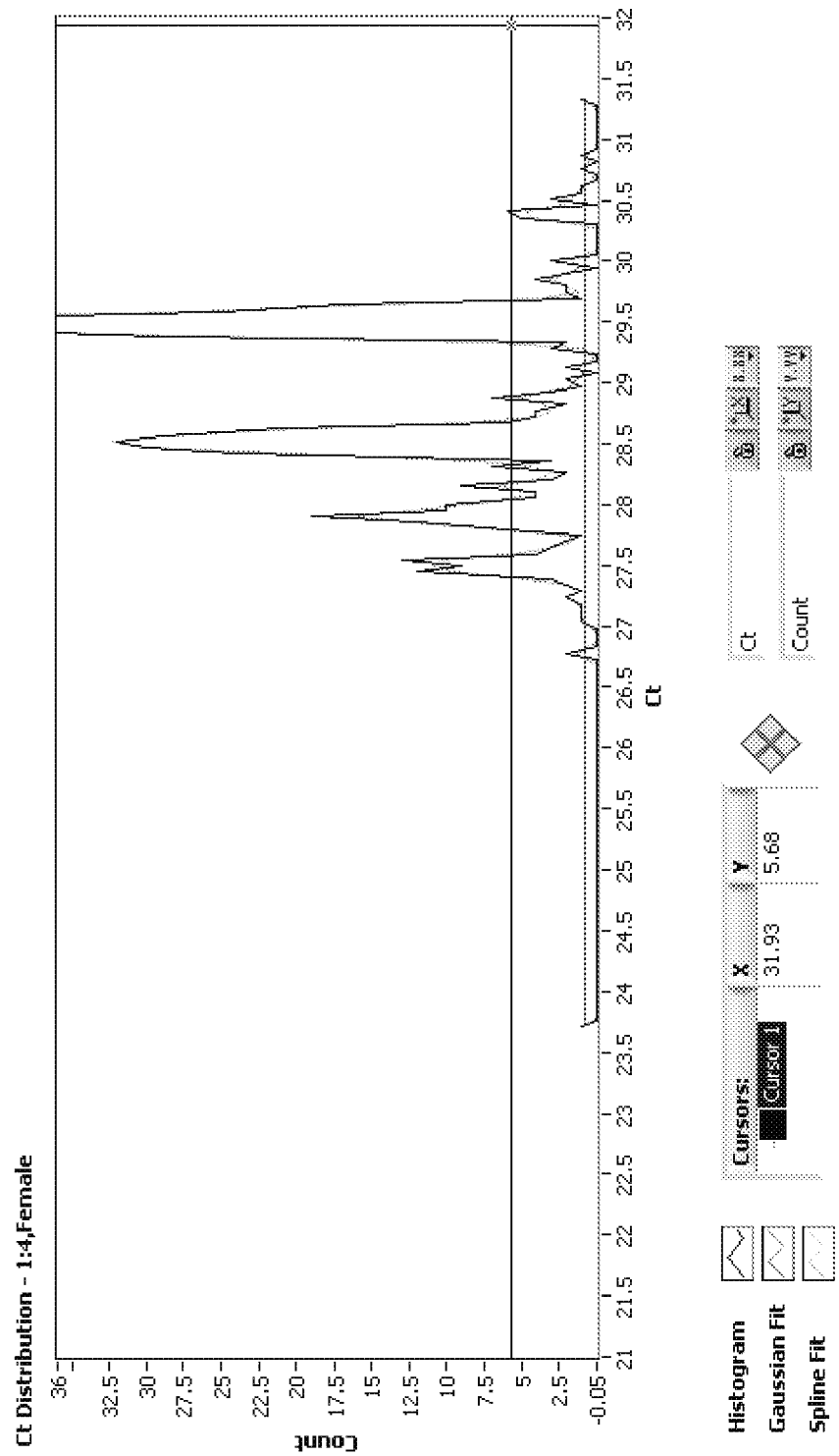
Figure 26:
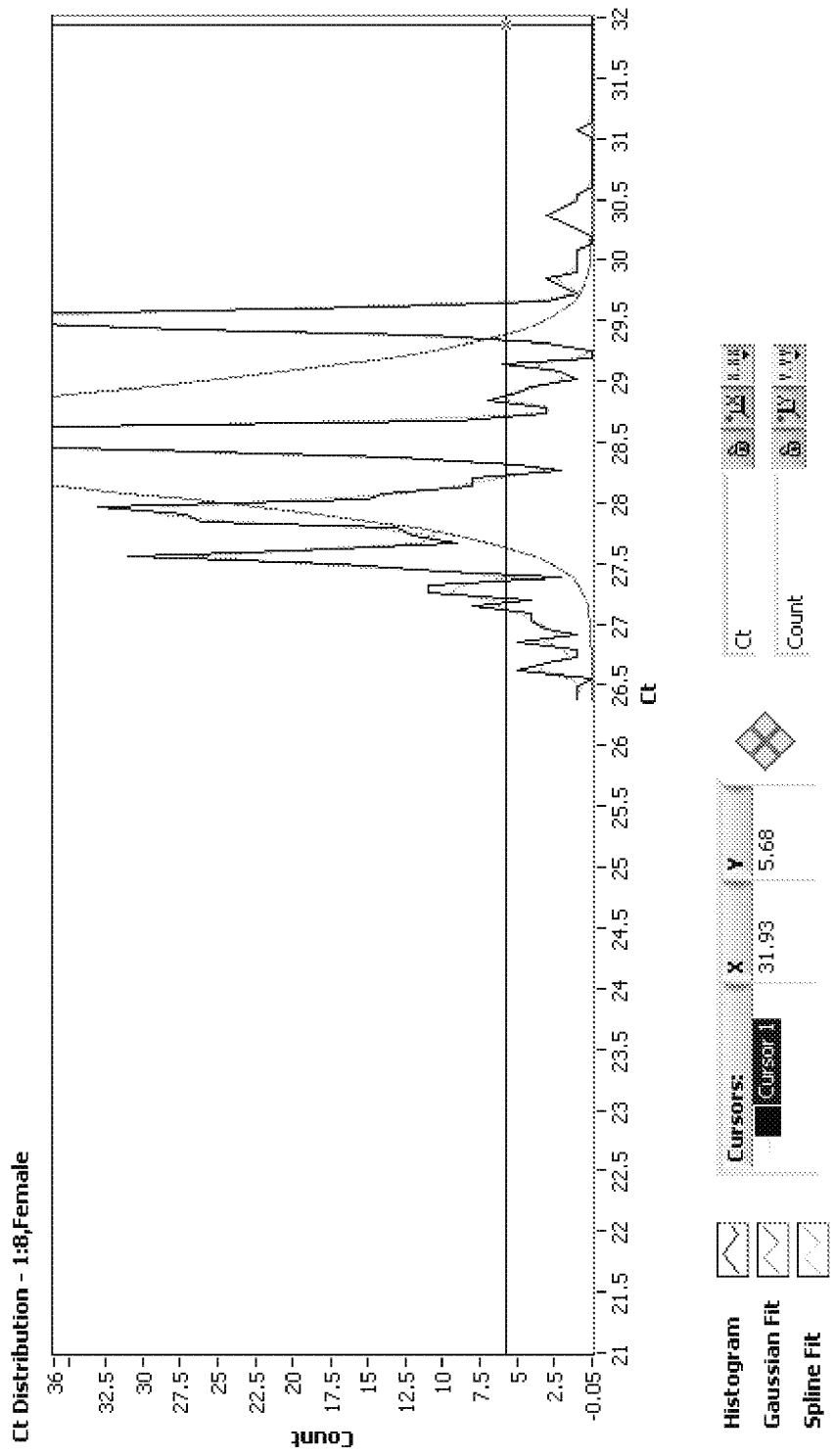
Figure 27:
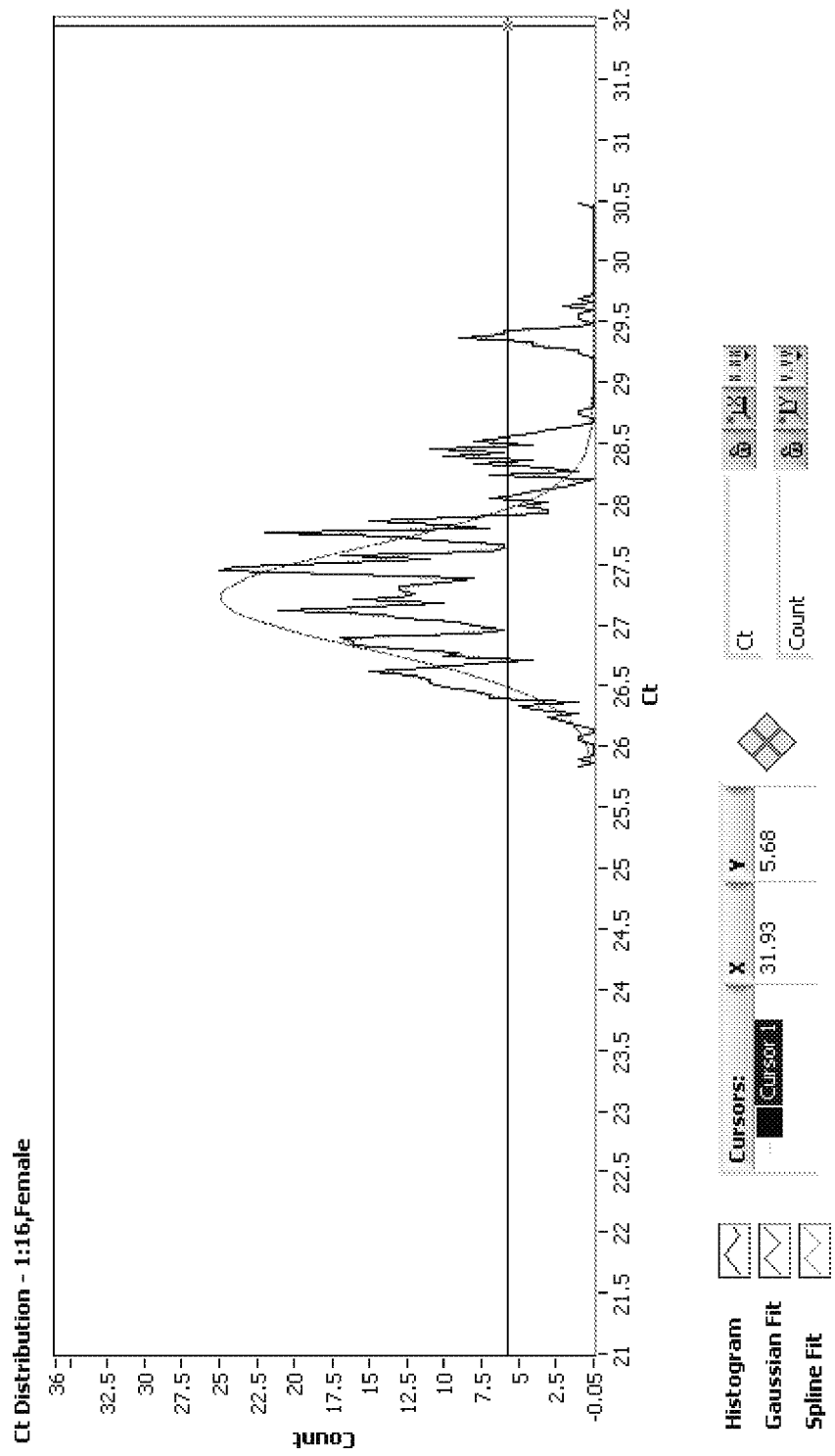
Figure 28:
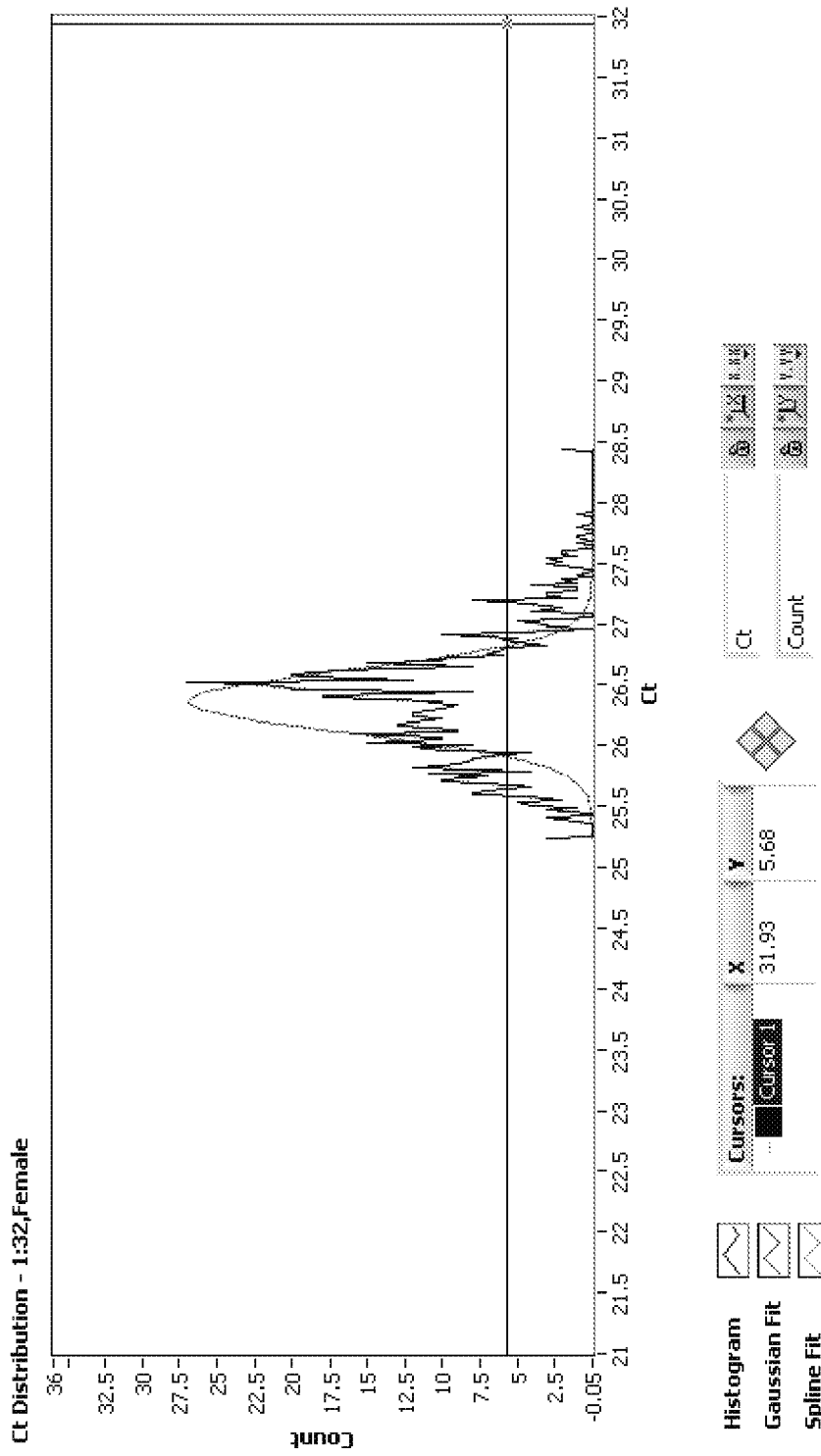
Figure 29:
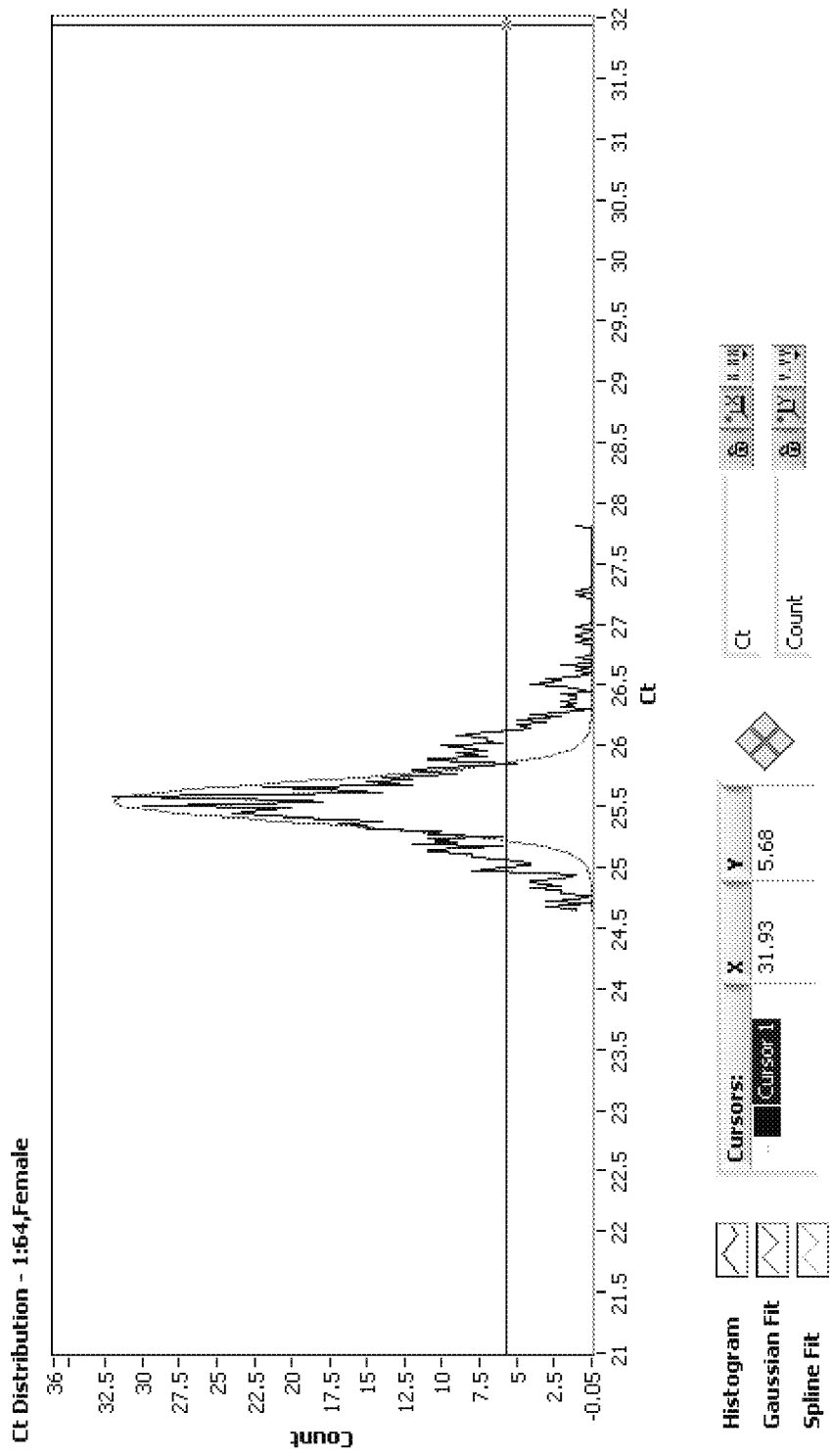
Figure 30:
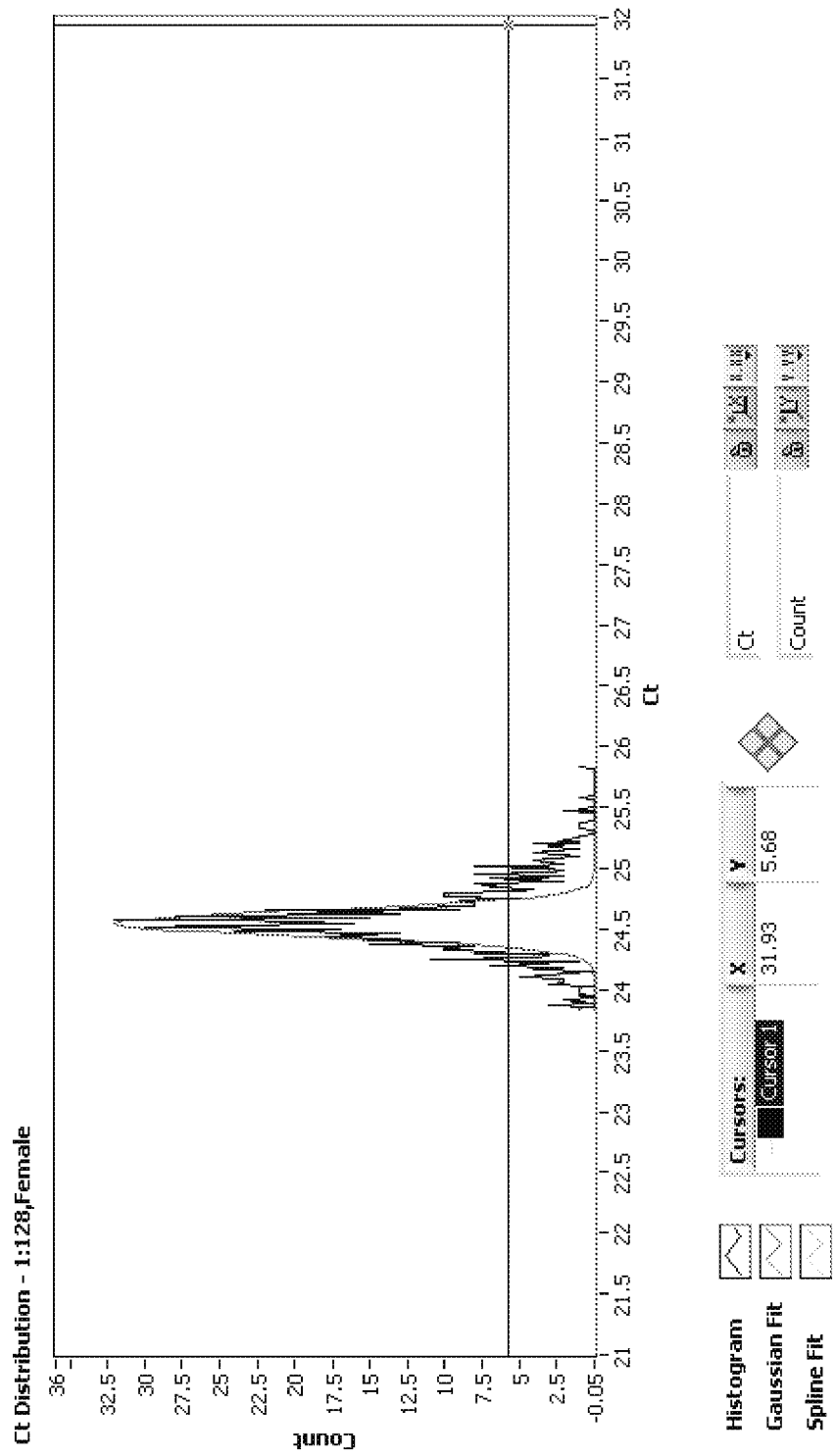
Figure 31:
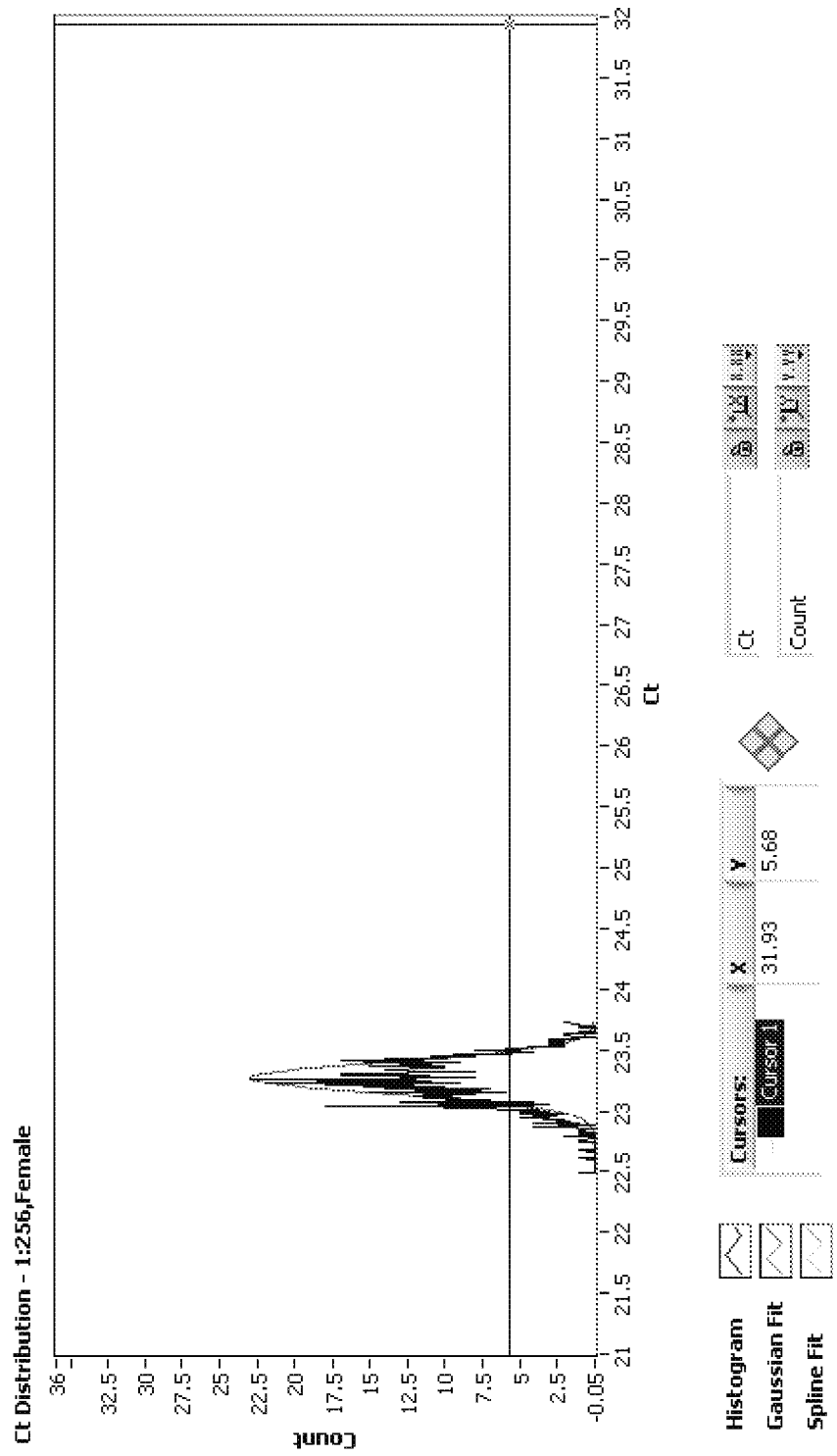
Figure 32:
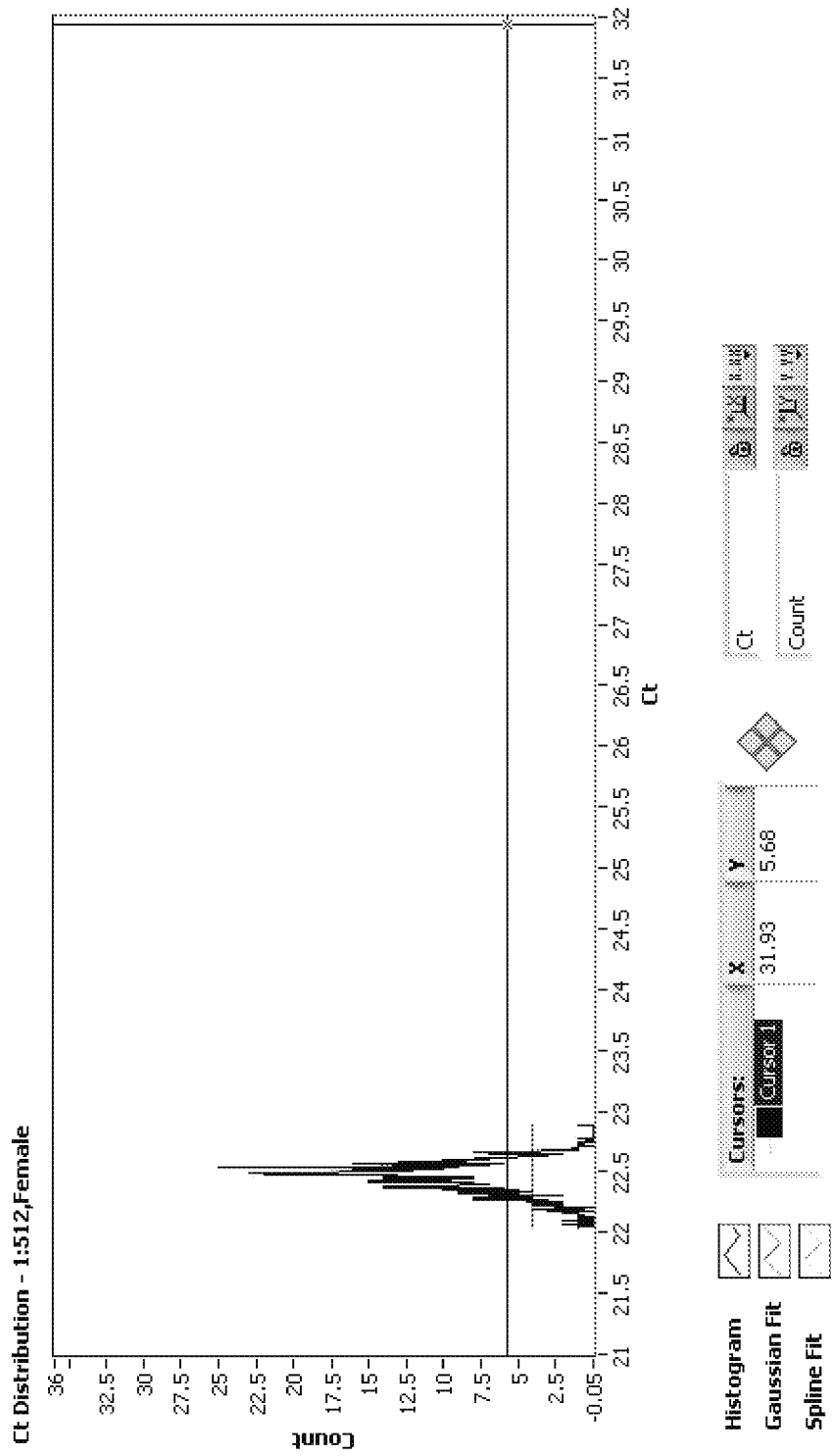

As described above, the aqueous droplets form a layer on top of the fluorocarbon fluid and are covered by the mineral oil. For subsequent analysis of the individual aqueous droplets, it is desirable to sample only the aqueous droplets and the fluorocarbon fluid, and to remove the mineral oil from the sample. An exemplary method is described below, with reference to FIG. 9.

In step 1, a capillary is inserted into a tube. The bottom end of the capillary is in the fluorocarbon phase and close to the bottom of the tube. In step 2, the fluorocarbon fluid 902 is withdrawn by applying negative pressure inside the capillary. The fluorocarbon fluid 902 goes into the capillary, followed by the aqueous droplets 904, and then the mineral oil 906. Next, the negative pressure is stopped when only a small amount of mineral oil 906 enters the capillary.

In step 3, the capillary is in the upright position. Because the aqueous droplets 904 have much lower density than the fluorocarbon fluid 902, they will float up until reaching the top of the fluorocarbon fluid 902. The mineral oil 906 inside the capillary tube forms a "plug" under the fluorocarbon fluid, but it does not float up. Thus the aqueous droplets 904 and the mineral oil 906 are separated automatically. Additionally, aqueous droplets 904 may be sorted by size because large aqueous droplets have much higher rising velocity than smaller aqueous droplets. In some embodiments, a variable amount of backflow can be applied to prevent small droplets from migrating up the capillary.

In step 4, sampling, the system can be backflushed to remove residual droplets and mineral oil.

EXAMPLE 2

In this example, the emulsion sample described above in Example 1 is used to test the sampling procedure. The emulsion held in an individual well on a 96-well PCR plate. The volume of the fluorocarbon fluid (HFE 7500) plus that of the aqueous droplet layer is 60 uL. The volume of the hydrocarbon oil (heavy mineral oil) is 40 uL. Thus, the total sample volume in the well is 100 uL.

A GASTIGHT® syringe (Hamilton #81320) is used together with a syringe pump (Nexus 3000) to provide negative and positive pressure. The inner wall of a capillary (I.D. 1 mm, length 10 mm) is coated with hydrophobic fluoropolymer coating. This is to prevent the wetting of aqueous droplets on the inner wall. An open end of the capillary is connected to the syringe needle via flexible silicone tubing.

In step 1, the capillary was kept upright and the other open end is inserted into the well containing the 3-layered emulsion assembly. The position of this end was inside the fluorocarbon fluid and close to the bottom of the tube, as shown in the attached sketch.

In step 2, the "withdraw" mode of the syringe pump was used to create negative pressure. The total volume to be withdrawn was set to be 70 uL and volumetric rate is set to 10 uL/min. At the end of this step all the fluorocarbon fluid and all the droplets were collected into the capillary, and only a small fraction of mineral oil (about 10 uL) was also collected. The pump was then stopped and no more oil was collected.

In step 3, the capillary was kept upright for 1 min. It was seen that majority of the aqueous droplets float to the top of the fluorocarbon fluid, and the bottom section of the fluorocarbon fluid became free of droplets. The mineral oil "plug" stayed under the fluorocarbon fluid.

In step 4, the "infuse" mode of the syringe pump was used to apply positive pressure inside the capillary. The volume to be infused was set to be 15 uL and the volumetric rate was 10 uL/min.

The mineral oil was pushed out of the capillary, and some fluorocarbon fluid was also pushed out. At the end of step 4, the sample inside the capillary contained only aqueous droplets and fluorocarbon fluid. The mineral oil was separated from the sample.

In the embodiments described above, a polydispersed water-in-fluorocarbon emulsion is created directly inside a common 96-well PCR plate covered by a lighter oil without an additional step. Aqueous droplets can are sampled, sorted and analyzed by buoyancy without flow.

As described, embodiments of these methods reduce the evaporation of aqueous droplets. Furthermore, the cover oil is added together with aqueous reagents and fluorocarbon fluid before emulsification. Eliminating extra step to open the emulsion vessel to add covering oil after emulsification is avoided. Moreover, the covering oil can be removed from the emulsion sample and will not interfere with sample analysis.

In other embodiments, the plurality of discrete sample portions may include using non-magnetic beads, magnetic beads, or a combination thereof may be used in the emulsion mix. In some embodiments, the plurality of sample portions may comprise non-magnetic beads, including porous or hollow beads, for example. The porous or hollow beads may be spherical or cylindrical. In some embodiments, no beads are used.

Detection of Positive or Negative Amplification

According to various embodiments, flow cytometry (FC) is used to count the number of droplets exhibiting specific fluorescence signals due to, for example, fluorescently-labeled nucleotide probes or antibody tags. The flow cytometry system can provide a fluid flow of suspended reactor droplets through an analysis region in which an excitation and detection system may be used to serially count the number of droplets with one or more specific fluorescent emission characteristics. Multi-color FC systems may be used for labeling or tagging droplets and/or target molecules with different markers.

TAQMAN® fluorescent probes, SYBR®, LUX®, or other real-time fluorescence detection methods may be used. If beads and SYBR® are used, and the method further comprises a flow cytometry step, SYBR® may subsequently be included in the running buffer of a flow cytometer to bind and label beads containing dsDNA. If beads and TAQMAN® are used, probes may be attached to the beads following cleavage. In some embodiments, labeled primers, such as LUX® primers, may be used to label beads, and the method may allow multiplexing without a need for using a dye-loaded buffer in a flow cytometry step.

According to various embodiments, a passive reference or spectator reference can be used in the method, for example, included in the aqueous amplification reagent mix. For bead-based approaches, the passive reference may be made to attach to the bead during or after the amplification, for example, prior to breaking the emulsion. In an exemplary embodiment, a biotinylated fluorescent ROX™ dye is used with a streptavidin-terminated bead. For non-bead-based emulsions, a water-soluble dye, such as ROX™ dye, may be used.

The present teachings expand the capabilities of dPCR by greatly increasing the number of replicates that may be processed in a given time period when compared to current dPCR methods. The improvements may be use available instrumentation and overcome the limitations of current m×n dPCR configurations. In some embodiments, the present teachings provide serial processing using conventional flow cytometry systems applied to dPCR. In some embodiments, the system and method processes micelles containing PCR reactants and dispersed in a substantially immiscible carrier fluid. In some embodiments, magnetic focusing is used in conjunction with flow cytometry and post-read, downstream collecting and processing of single droplets is enabled.

According to various embodiments, emulsion PCR (emPCR) is used and may involve a massively parallel PCR amplification of nucleic acid samples in aqueous reactors immersed in a substantially immiscible continuous phase, for example, in a non-soluble oil medium. The method may be used, for example, to prepare poly-disperse collections of reactor droplets or libraries for analysis.

According to various embodiments, fluorescent-activated cell sorting is used such that, following analysis, various fluid manipulation methods divert droplets with specific fluorescence signatures to different locations or chambers for enrichment or other further processing.

According to the present teachings, a system and method are provided for using emulsion PCR with a flow cytometry read-out to provide a digital PCR answer. Unlike conventional flow cytometry systems and methods that process cells, the "cells" in the present flow cytometer system are instead individual PCR reactant-containing droplet reactors, some of which may comprise replicates of PCR reactions, also referred to as positive results.

In various embodiments, following the formation of the discrete sample portions, the resulting amplification products can be introduced into a flow cytometer. This can be accomplished in any suitable way. For example, when beads are used, the emulsion can be broken with detergent, rapid aqueous dilution, or another standard emulsion breaking method. An aqueous suspension of the beads can then be introduced into a flow cytometer in a manner similar to how cells are typically loaded in a conventional cell manipulating flow cytometer. In some embodiments, for bead and bead-less emulsions, lipids may be included in the emulsion followed by aqueous dilution to result in micelle formation, wherein the PCR product may be contained, for example, within a lipid bilayer. Such a droplet can be referred to as a "PCR cell" that may then be introduced and analyzed in a manner used to introduce and analyze a conventional biological cell in a flow cytometer.

Plates of emulsified samples can be bulk thermal cycled using a standard thermal cycler, for example, using any of the many thermal cyclers available from Applied Biosystems, LLC of Foster City, Calif., for example. Furthermore, as used herein, thermal cycling may include using a thermal cycler, isothermal amplification, thermal convention, infrared mediated thermal cycling, or helicase dependent amplification, for example. In some embodiments, the chip may be integrated with a built-in heating element.

Amplification may be run to completion to create strong signals for the reporters present in droplets containing a target molecule. In some embodiments, a microfluidic meandering PCR method may be used or isothermal amplification techniques may be used to keep emulsions intact.

According to various embodiments, the method may comprise subjecting the plurality of discrete sample portions to nucleic acid amplification conditions for carrying out a polymerase chain reaction, for example, thermal cycling conditions.

In some embodiments, the flow cytometer can be set to detect at least two colors, for example, the passive reference and the indicator dye. In an example, the flow cytometer may be set up to detect fluorescence from a SYBR® dye and from a FAM™ dye. Using TAQMAN® fluorescent probes available from Applied Biosystems, LLC of Foster City, Calif., multiplexing can also be applied generating more than one probe signal, for example, to generate signals form FAM™, VIC®, and other dyes. For simplex reactions, 3 types of "cells" should be distinguishable: unlabeled cells from beads/micelles which were not in contact with the sample-PCR mix, cells labeled with the spectator dye only from beads/micelles which included PCR mix but no template, and cells labeled with both dyes, where the bead/micelle was in contact with both the PCR mix and a target template.

A digital read-out may be calculated as follows. Two-dye "cells" are 1 (indicating mix+template present), passive dye-only "cells" are 0 (indicating mix but no template), and un-dyed "cells" are not used in the calculation. The number of 0 and 1 "cells" is used to fit the Poisson equation, and estimate the number of template molecules present in the original diluted sample. From that, the number of template molecules present in the original undiluted sample can also be estimated.

According to various embodiments, magnetic beads may be used in the assay. Magnetic forces may be used to break the emulsion. Cylindrical solenoid fields may be used during flow cytometry to focus beads into the center of the flow stream, increasing the sensitivity and throughput of the flow system. In some embodiments, focusing may be enabled by an acoustic focusing system as described below. Following analysis, variable magnetic fields can be used to direct particular "cells" to an appropriate reservoir.

In some embodiments, if non-magnetic beads are used in the emulsion, a magnetic passive reference may be included in the PCR mix. For example, iron nanoparticles may be used which are functionalized for aqueous solubility and covalent attachment to polystyrene beads, silica beads, or other beads. In this way, a magnet can be used to retain beads which are exposed to the reaction mix (true PCR positives and negatives) while beads which were not exposed to the mix during formation may be easily washed away. Such an approach may also be used to facilitate clean-up for SOLiD™ library preparation.

By using an acoustic focused flow system, as in some embodiments, a method is provided that has very high speed and flexibility. Also very low sheer can help keep the emulsion intact during the reading process, as opposed to higher sheer that might disrupt the emulsion and cause inaccurate results. The present systems and methods can measure up to 1,000,000 discrete sample portions per sample, for example, from about 1,000 to about 1,000,000 discrete sample portions per sample, from about 10,000 to about 1,000,000 discrete sample portions per sample, or from about 100,000 to about 1,000,000 discrete sample portions per sample.

Exemplary acoustic flow systems and methods and components thereof that can be used in the present systems and methods include those described, for example, in U.S. Published Patent Applications Nos. US 2009/0050573 A1 to Ward et al. and US 2009/0178716 A1 to Kaduchak et al., both of which are incorporated herein in their entireties by reference. Other flow cytometry systems and methods having components that can be used in the present teachings include those described, for example, in U.S. Published Patent Application No. US 2009/013066 A1 to Oldham and in U.S. Pat. No. 7,280,207 B2 to Oldham et al., both of which are also incorporated herein in their entireties by reference.

Fluorescent-Activated Cell Sorting (FACS)

Determining a presence or an absence of the at least one target nucleic acid in each of the plurality of processed sample portions may comprise measuring a fluorescence signal. After determining the presence or absence of the at least one target nucleic acid in each of the plurality of processed sample portions, fluorescent-activated cell sorting (FACS) may be used to sort the plurality of processed sample portions according to the fluorescent signal measured. In some embodiments, the volume of one or more of the processed sample portions may be estimated by measuring a fluorescence signal. The determining a presence or an absence may comprise introducing each of the plurality of processed sample portions individually into a flow cytometer.

If a FACS platform is used, after flow through the analysis region, a bead/micelle can be segregated according to the fluorescent signals detected. For example, all positive beads can be shunted, directed, or diverted to a separate reservoir for collection and subsequent downstream analysis with other methods, for example, for a sequencing reaction or a sequence detection reaction.

The system and method provide the ability to estimate the droplet volume, as well as the presence of a reporter for PCR amplification. For this purpose, a flow cytometer such as a modified acoustic focusing flow cytometer may be used with an autosampler. The flow system may autosample from 96- or 384-well plates. Acoustic focusing may be sued to enable excellent focus control and can achieve read speeds of 20,000 events per second. The size of a droplet can be measured using any of a variety of properties of the droplet, for example, by measuring laser forward or side scatter properties. In some embodiments, a reference dye may optionally be added to the aqueous phase, and the signal from the reference dye may be used to estimate droplet volume. Positive and negative counts are available for each droplet that passes the laser interrogation zone in the center of the acoustically focused flow. High throughput using parallel acoustic focusing streams may be achieved. Sorting positive droplets may be employed as a preparatory method for DNA sequencing.

Non-Flow Cytometry Read-Out Alternatives

In some embodiments, read-out methods after emPCR are used that are alternatives to flow cytometry. For example, emulsion products with beads can be dispersed on a glass slide, for example, containing a thin gel matrix for immobilization. The dispersed, fluorescent beads can be read using a SOLiD™ platform (available from Applied Biosystems, Foster City, Calif.), a conventional fluorescence microscope, or a COUNTESS™ cell counting system available from Invitrogen, Carlsbad, Calif. The presence of passive reference-only beads indicates the stochastic limit has been reached, and these beads do not need to be quantified. Counting the number of positive beads then provides quantitation of the template molecules present in the initial mix. Micelles and/or beads may also be read serially using Capillary Electrophoresis systems with polymer (or no polymer), for example, using a polymer specially optimized for such reactors.

According to various embodiments, a system that uses a manual PCR setup is provided that may use SYBR® or TAQ-MAN® assays and standard qPCR SuperMixes. The reactions may be set up in a standard 96-well plate using typical PCR volumes, for example, from about 5 µL to about 15 µL, covered with approximately 50 µL of oil or fluorinated fluid for emulsion PCR. The plate may be sealed using an adhesive cover. More complicated microfluidic reaction assemblies may also be used.

Dilution and Fluorescent-Activated Cell Sorting (FACS)

The present teachings can achieved a throughput of thousands of sample droplets per minute. As a result, the dynamic range of an assay may be expanded and the method can be extended to applications typically reserved for qPCR, such as gene expression, genotyping, and miRNA analysis. The present systems and methods are well suited for small sample inputs, for example, single cell samples. In some embodiments, a fluorescent-activated cell sorting (FACS) system is used and the method may comprise collecting and purifying selected post-PCR samples from other samples, obviating the need for user accessibility to and manipulation of samples in plate or array formats. For example, all mutant amplicons identified by dPCR may be sorted from wild-type amplicons, for subsequent sequencing.

In some embodiments, the method involves using FACS before and after emPCR. Prior to emPCR, the FACS can be used to prepare and isolate single cells (or types of cells) for analysis. The single cells can be lysed and introduced into the emPCR step for subsequent FC analysis. As an example, circulating tumor cells, as detected by a fluorescent antibody, may be counted and enriched by FACS. The resulting cancer cell product can then be analyzed using the dPCR approach described above, that is, emPCR followed by FC/FACS, which provides an extremely low limit of detection for quantifying expression levels in these purified cells.

The fraction of beads/micelles containing neither passive reference nor template may be large if the emulsion PCR process is not optimized. With a throughput of 10,000 cells per minute, if 10% of beads/micelles are in contact with the PCR mix, 60,000 usable digital replicate results may be obtained in one hour of flow cytometer time. Moreover, the emPCR+FC of the present teachings can produce answers beyond typical dPCR results. For example, the method may be used to simply genotype a sample by measuring the ratio of the FAM/ROX cells and the VIC®/ROX™ cells. In some embodiments, with such a high throughput, a 3-5 log dynamic range may be attainable for gene expression or miRNA analysis. Using this approach, with 60,000 observations per hour, roughly 1,000-fold differences in expression of two targets may be measured. For example, 21,045 cells of target A vs. 24 cells of target B may be quantified, a 1000-fold difference in expression levels measured which is absolute in quantity and independent of PCR efficiency and other differences between the two targets.

Volume Estimation of Discrete Sample Portions

In yet other embodiments of the present teachings, an alternative data analysis method for absolute target molecule quantification from heterogeneously sized dPCR reactions, is provided. The method may comprise determining absolute target concentrations from reactions of various volumes. The reactions may be created with random sizes, randomly or deliberately. The method is useful in analyzing dPCR data from polydisperse emulsions, such as emulsions created with mechanical or sonic energy.

The method may further comprise comparing the plurality of processed portions to a plurality of standards of known respective volumes, for example, a plurality of standards of known respective volume that uniformly sized or that are of different known volumes. The method may further comprise subjecting a plurality of portions of a standard to the same nucleic acid amplification conditions to form a plurality of processed standards, wherein each of the processed standards are of a known respective volume, and then comparing the plurality of processed standards to the plurality of processed sample portions. In some embodiments, the plurality of sample portions have an average of from about 0.1 to about 0.8 copy of the target nucleic acid per discrete loaded mixture. The plurality of sample portions may have an average diameter of from about 0.3 micrometer (µm) to about 600 µm, or an average diameter of from about 1.0 µm to about 100 µm, or an average volume of from about 0.5 femtoliter (fL) to about 1 microliter (µL), or an average volume of from about 10.0 fL to about 100 nanoliters (nL).

Figure 6:
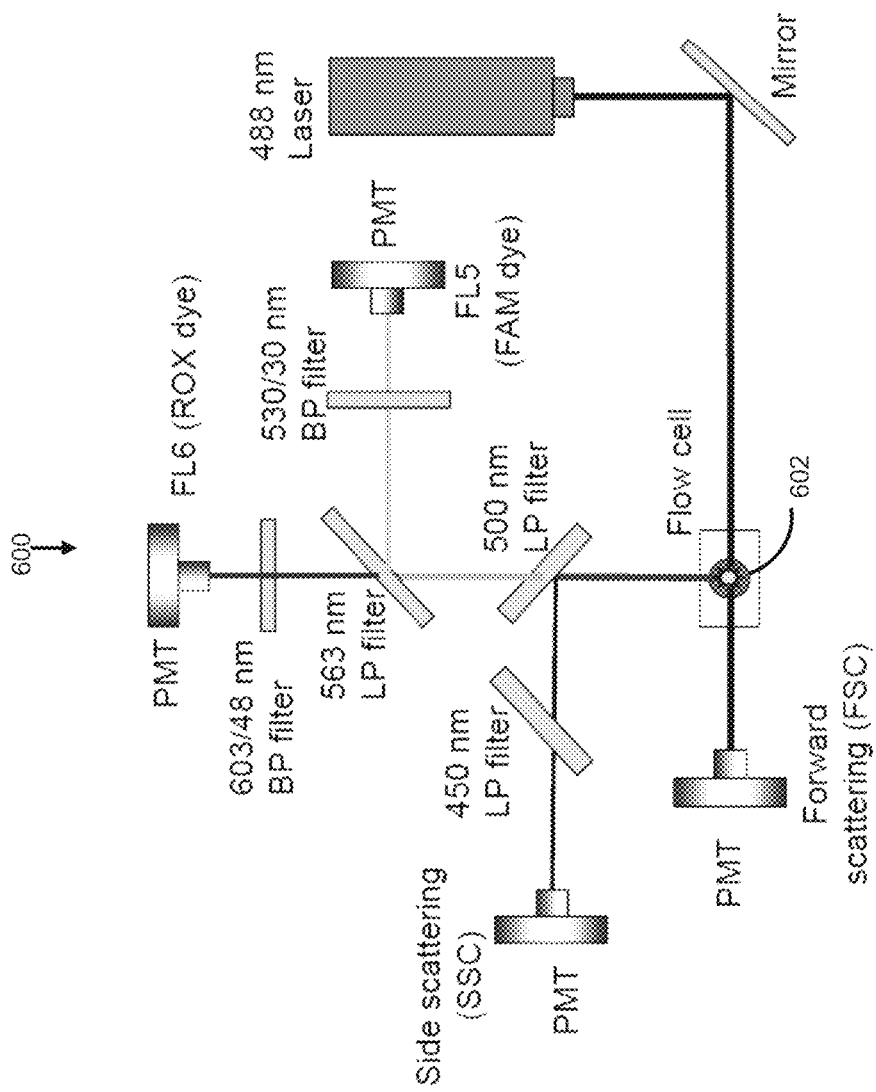
FIG. 6 illustrates an exemplary optical setup using flow cytometry to analyze a plurality of discrete sample portions according to various embodiments of the present teachings.
Figure 7B:
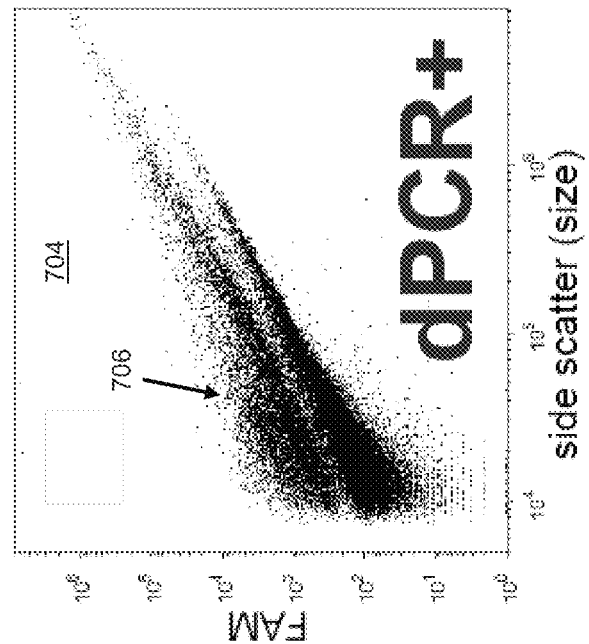
FIG. 7B illustrates flow data of samples including a template control according to various embodiments of the present teachings.
Figure 7A:
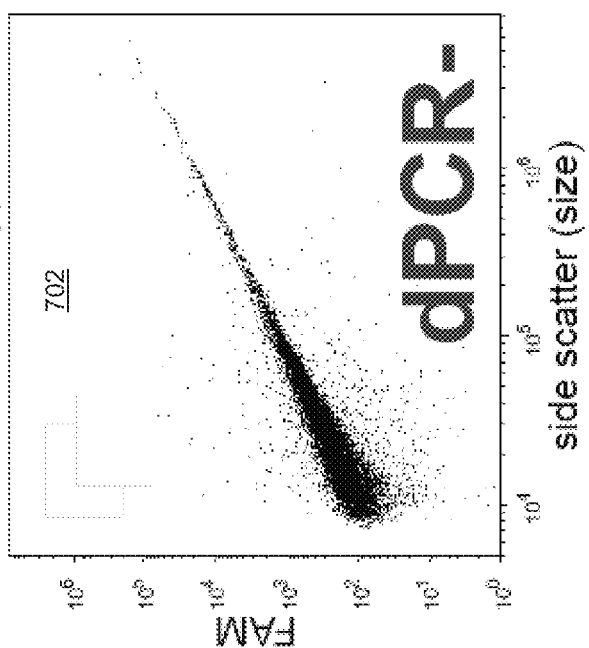
FIG. 7A illustrates flow data of samples that included no template control according to various embodiments of the present teachings.

According to various embodiments, the volume of the discrete sample portions is estimated. The present systems and methods may use an optical imager for using optical scatter properties, a passive reference dye, optical refraction properties, optical imaging for measurement, optical reflection properties, optical absorbance properties, optical transmission properties, a ladder of standard droplet sizes using different reference dyes, or a combination thereof to estimate discrete sample portion volumes. An exemplary optical imager 600 is depicted in FIG. 6 to detect samples in flow cell 602. An optical imager may also be camera configured to take images of the discrete sample portions, for example.

In an example, discrete sample portions of first, second, and third volumes of different known respective standard sizes may contain first, second, and third respective detectably unique dyes and may be identified and used to scale the size of the discrete sample portions having unknown volume sizes. The systems and methods of the present teachings may produce discrete sample portion sizes of from about 0.3 µm in diameter up to about 1000 µm in diameter, for example, from about 0.4 µm in diameter up to about 300 µm in diameter, from about 0.5 µm in diameter up to about 200 µm in diameter, or from about 1.0 µm in diameter up to about 100 µm in diameter. Discrete sample portion volumes of up to about 1.0 µL in size may be produced and processed according to various embodiments. Discrete sample portion volumes based on spherical diameters can be estimated, for example, using a conversion chart such as this one:

| Radius | diameter | volume | |
|--------|----------|--------|--------|
| 0.6 uM | 1.2 uM | 1 fL | e. coli |
| 1.4 uM | 2.8 uM | 10 fL | |
| 3 uM | 6 uM | 100 fL | |
| 6 uM | 12 uM | 1 pL | |
| 14 uM | 28 uM | 10 pL | human cell |
| 30 uM | 60 uM | 100 pL | |
| 60 uM | 120 uM | 1 nL | |
| 140 uM | 280 uM | 10 nL | |
| 300 uM | 600 uM | 100 nL | |
| 600 uM | 1200 uM | 1 uL | |

Measuring the size of each of the plurality of processed sample portions may comprise analyzing each of the plurality of processed sample portions, and the analyzing may comprise one or more of measuring or analyzing an index of refraction, a light scattering property, a forward light scattering property, a side light scattering property, an optical absorption property, an optical transmission property, a peak height of an optical signal, a peak width of an optical signal, a fluorescent property, a time-of-flight fluorescent property, or a combination thereof. The method may further comprise estimating what size of processed sample portion provides a specific percentage of processed sample portions of that size that test positive for the presence of one or more of the at least one target nucleic acid, or estimating what size processed sample portion of the differently-sized processed sample portions provides a 50% positivity rate with regard to determining the presence of one or more of the at least one target nucleic acid.

Estimating Number of Copies-Per-Unit-Volume of Sample

According to yet other embodiments of the present teachings, a method for estimating the number of copies-per-unit-volume of at least one target nucleic acid in a sample is provided. The method may comprise: forming a plurality of discrete sample portions each comprising a portion of a sample, and a reaction mixture; subjecting each of the plurality of discrete sample portions to nucleic acid amplification conditions to form a plurality of discrete processed sample portions including at least one discrete processed sample portion containing nucleic acid amplification reaction products; generating and measuring fluorescence signals from at least some of the plurality of discrete processed sample portions; analyzing each of the plurality of discrete processed sample portions individually to determine a presence or an absence of one or more of the at least one target nucleic acid in each of the plurality of discrete processed sample portions based on the fluorescence signals, and to determine the respective volumes of the plurality of discrete reacted mixtures; and estimating the number of copies-per-unit-volume of the at least one target nucleic acid in the sample based on (1) the number of discrete processed sample portions determined to contain one or more of the at least one target nucleic acid present therein, and (2) the determined respective volumes. Each of the plurality of discrete sample portions may be provided in a multi-well plate and the method may further comprise emulsifying to form the plurality of discrete sample portions.

In some embodiments, the method further comprises estimating what size of processed sample portion provides a specific average number of copies-per-unit-volume, or estimating what size processed sample portion of the differently-sized processed sample portions provides an average of from 0.25 to 0.75 copy-per-processed sample portion.

Bayesian Inference to Concentration Estimation

According to various embodiments, an algorithm may be used for estimating target concentration within a dPCR system with multiple discrete sample portions sizes and/or multiple sample dilutions and/or low precision in resolving positive and negative amplification reactions. Typically, data analysis methods for digital PCR systems are based on a strict set of assumptions that may not be possible to meet in practice, or may even be undesirable. For example, typical assumptions may be: all dPCR discrete sample portions have identical volume, all dPCR discrete sample portions have identical sample dilution, and the distinction between positive and negative discrete sample portions can always be made with very high precision If any of the above assumptions are violated in a practical system, by design and/or due to system imperfections, for example, following standard data analysis methods may lead to suboptimal results.

According to various embodiments, methods of data analysis may be utilized that explicitly takes into account that discrete sample portions have varying/uncertain volumes and concentrations, and account for measurements of varying quality. This may be achieved by estimating the target concentration through Bayesian inference, although other statistical estimation techniques are also appropriate.

Some of the following assumptions may need to be incorporated into the model statistically linking target concentration to measurements: treating discrete sample portion volumes as constants, specified separately for each discrete sample portion, or treating discrete sample portions volumes as random variables with known distributions (obtained by characterizing or calibrating the system), or treating discrete sample portion volumes as random variables with known conditional distributions, dependent on volume dependent measurements obtained at the run time, such as discrete sample portion diameter estimate, discrete sample portion area estimate, passive reference intensity, etc.

One assumption may be treating discrete sample portion concentrations as constants, specified separately for each discrete sample portion, or treating discrete sample portion concentrations as random variables with known distributions, obtained by characterizing the system and dilution preparation protocol.

Another assumption that may be made is treating end-point intensity reads as random variables with known "positive" and "negative" distributions, obtained by characterizing the measurement system.

A goal of Bayesian inference is to produce posterior probability distribution of target concentration, conditional on all available information and measurements. Such posterior distribution may then be used to derive maximum likelihood estimate, unbiased estimate, and/or confidence interval for target concentration.

Central to these methods, according to various embodiments, is a score function that depends on both the observed results and a specific value of the target concentration. The score function conveys information on how good the agreement between a hypothetical value of the concentration and the actually observed measurements. In other words, a value of the score function obtained for certain concentration and certain measurements is a measure of the likelihood that these measurements could arise if the sample under consideration indeed had this concentration.

Maximum Likelihood Estimation

In one embodiment, the process of estimating the target concentration involves finding the value of concentration for which, given a set of measurements, the score function attains the maximum value (or appropriately high value; or value appropriately close to maximum). This search for maximum value may be performed by evaluating the score function on a predefined set of candidate solutions and choosing the maximum, a successive approximation method, evaluating the analytical solution to the maximization problem, or any number of other maximization method or combination of methods.

Unbiased Estimation

In another embodiment, the process of estimating the target concentration involves finding the weighted average of candidate concentration values (the candidate values coming from a predefined or dynamically established set of discrete of continuous concentration values), where the values of the score function (obtained for the candidate concentrations) serve as the weights in the averaging process. This process can be achieved by evaluating the score function for all or subset of candidate values and directly calculating the weighted average; or by evaluating an analytical solution; or by any other appropriate method.

Confidence Interval

In addition to producing the estimate of the target concentration, a confidence interval may be generated. The confidence interval is a range of target concentration values, delimited by the upper value and lower value, calculated from the measurements, such that the likelihood that the true target concentration value is outside of this range is small. For example, a 95%-confidence interval is where the model-based probability of true target concentration being outside of it is 5%. The confidence interval can be established as the range of target concentration values for which the score function is above certain threshold. The threshold may be dynamically calculated. For example, the threshold may be selected such that the sum (or integral) of score function values exceeding the threshold is greater by a predefined factor from the sum (or integral) of score function values below the threshold. (for example, if the score function is in fact a model-based likelihood function and 95%-confidence interval is sought, the threshold is selected so that the integral of likelihoods above the threshold is 95/5 times greater that the integral of likelihoods below the threshold).

Score Function

In some embodiments, the score function can be: a measure of probability; a measure of conditional probability; a measure of likelihood; a logarithm of probability. The score function may use the following probabilistic model that expresses the conditional probability of the positive/negative measurements for individual PCR reactions conditioned on the target concentration and volumes of the PCR reactions. Alternatively, the score function may be a model-based conditional probability of fluorescence measurements for individual PCR reactions conditioned on the target concentration and on volume measurements for the PCR reactions.

Under the constraint on the total number of droplets, digital PCR systems with multiple droplet sizes and/or multiple sample dilutions can carry significant dynamic range advantage over system with equally sized and diluted droplets. However, such a system may need much different data analysis to determine target concentration in the original sample. For example, the system may need to take into account discrete sample portion volumes and dilutions, dilution information may need to be provided by the user or is system-specific, or discrete sample portion volume information may be either provided or estimated at run time based on a size measurement, passive reference intensity, or features of real-time amplification curve, for example.

$\lambda$—true target concentration in undiluted sample
N—number of droplets
$V_i$—true volume of droplet i
$C_i$—true dilution coefficient of droplet i (what fraction of $V_i$ is taken up by the undiluted sample)
$W_i$—set of measurements or prior information about volume of droplet i
$D_i$—prior information about dilution coefficient of droplet i
$X_i$—true number of target molecules in droplet i
$Y_i$—plus/minus measurement for droplet i $$P(V_i \mid W_i)$$

$$P(C_i \mid D_i)$$

$$P(X_i \mid V_i, C_i, \lambda)$$

$$P(Y_i \mid X_i)$$

$$P(Y_i = 0 \mid X_i = 0) = 1 - f_p$$

$$P(X_i \mid V_i, C_i, \lambda)$$

$$P(Y_i \mid D_i, W_i, \lambda) = \int_0^\infty \int_0^\infty \sum_{N_i=0}^\infty P(Y_i \mid X_i) P(X_i \mid V_i, C_i, \lambda) P(C_i \mid D_i) P(V_i \mid W_i) dC_i dV_i$$

$$P(Y \mid D, W, \lambda) = \sum_{i=1}^N P(Y_i \mid D_i, W_i, \lambda)$$

$$\hat{\lambda}_{ML} = \operatorname*{argmax}_\lambda \prod_{i=1}^N P(V_i \mid D_i, W_i, \lambda)$$

Multi-Level Digital PCR

In another embodiment, the number of copies of the target nucleic acid may be estimated based on real-time measurements and $C_q$ values to discriminate between the number of starting template target nucleic acid copies. $C_q$ values are also referred to as $C_T$ values in some examples. In this way, accuracy and dynamic range of dPCR can be enhanced.

As described in various embodiments above, dPCR is based at least in part on partitioning the sample into a plurality of discrete sample portion, which may be viewed as a large number of separate PCR reactors. A positive/negative PCR test is performed on each PCR reactor, whereby each individual plus/minus test discriminates between zero starting copies and nonzero starting copies.

According to this embodiment, a method using $C_q$ values from each reactor is provided to achieve higher dynamic range and accuracy than would be possible from simple plus/minus calls.

As described above, a positive/negative data analysis is generally described as determining the number of positive and negative reactions. Then, making the assumption that the number of starting template copies per well follows Poisson distribution, it can be inferred the most likely total number of copies from the number of positive and negative wells.

According to this embodiment, a $C_q$-based dPCR data analysis method includes determining a number of negative reactions. For reactions that showed amplification, the most likely number of starting template copies from $C_q$ is determined. The relationship between $C_q$ and copy number can be determined by finding peaks in the $C_q$ histogram, with right-most peak corresponding to 1 copy, as illustrated in FIGS. 10-15. The method further includes determining the most likely total number of template copies by summing up template copy numbers from individual reactors.

Furthermore, for each well the likelihoods of starting copy number 0, 1, 2, etc, may be determined instead of making a copy number call. This can be used to determine a total number of copies more precisely with tighter confidence interval. Moreover, the process of associating $C_q$ with copy number may also assume Poisson copy number distribution and logarithmic spacing between $C_q$s.

As the result of using Cq-based dPCR with the above analysis according to embodiments described herein, better accuracy and dynamic range with the same number of reactors, and the same accuracy and dynamic range with lower number of reactors compared to plus/minus-based dPCR may be achieved.

Initial PCR Efficiency Determination from dPCT $C_q$ Spectrum

According to another embodiment, a method of measuring PCR efficiency in the first PCR cycle from the Cq spectrum of a dPCR experiment is provided. The method includes measuring the fraction of replicate PCR reactions with one copy of starting template that did not amplify in the first PCR cycle.

PCR efficiency can be described as the percentage of DNA template that produces a copy during a single PCR cycle. PCR efficiency is an important unknown parameter in downstream analysis of real-time amplification curves. PCR efficiency can differ between cycles of PCR, generally decreasing with each cycle. During real-time PCR, once the amount of PCR template exceeds the detection level, the fluorescence intensity can be used to monitor the rate of change of the template amplicon and thus to infer the efficiency.

However, this approach cannot be used to directly measure the efficiency at the initial cycles when the fluorescence is below detection level. It is common to make various assumptions about this initial efficiency, such as assuming 100% initial efficiency, assuming initial efficiency is the same as later, directly observed efficiency, or to use various models that extrapolate the initial efficiency backward from the observed efficiency.

According to this embodiment, the method includes using a target nucleic acid template dilution that targets the average number of starting template copies per reaction close to 1. This yields high fraction of reactions to have precisely one starting copy (assuming a Poisson-distribution across reactions). An amplification curve is collected for all reactions and $C_q$ values are obtained.

The method may establish the number of reactions A that had one starting target nucleic acid template copy and that copy was amplified in the first PCR cycle, and the number of reactions B that had one starting target nucleic acid template copy and that copy was not amplified in the first PCR cycle, but did amplify in subsequent PCR cycles.

Figure 33:
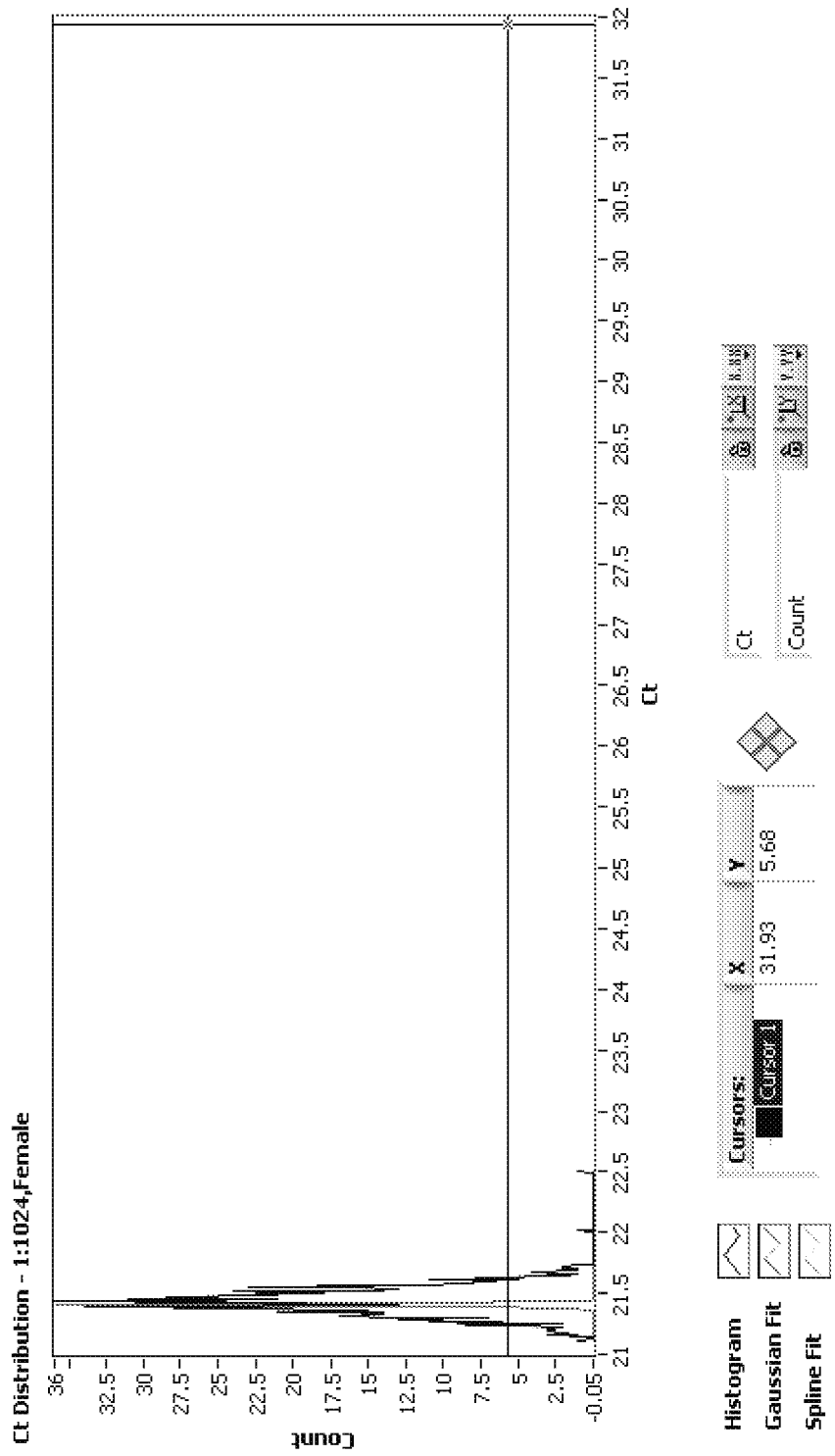
Figure 34:
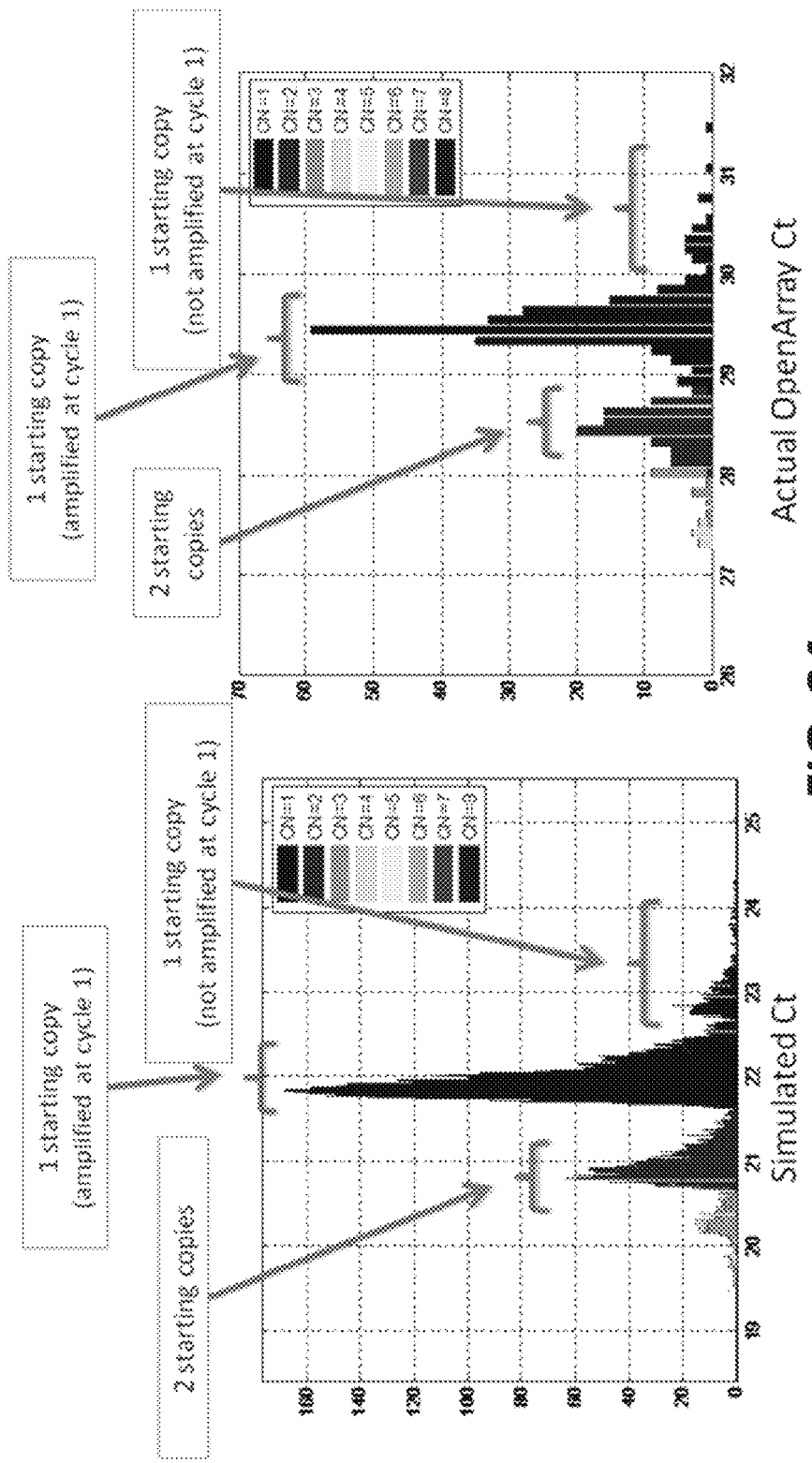
FIG. 34 illustrates an exemplary histogram for determining PCR efficiency according to various embodiments of the present teachings.

The cycle-1 efficiency can be then calculated as A/(A+B), where A and B are determined from the $C_q$ histogram. This is based on identification of the histogram peak corresponding to the groups A and B, which is illustrated in FIG. 33.

Furthermore, knowledge of the efficiency at the initial PCR cycle can be used as a reagent research and QC tool. Additionally, this method may also enhance our qPCR models possibly leading to improved accuracy of qPCR data analysis.

Also, as mentioned above, in various embodiments, the methods and systems described herein may be used to detect other biological components of interest. These biological components of interest may include, but are not limited to, cells and circulating tumor cells, for example. Furthermore, in addition to dPCR, the methods and systems in various embodiments may be used in applications, such as fetal diagnostics, multiplex DPCR, viral detection, genotyping, and rare allele detection copy number variation.

All publications, patents, and patent applications mentioned in this specification are herein incorporated by reference to the same extent as if each individual publication, patent, or patent application was specifically and individually indicated to be incorporated by reference.

While embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

The invention claimed is:

1. A method for quantification of a target nucleic acid in a sample, the method comprising:
    forming a plurality of discrete sample portions, each of the plurality of discrete sample portions comprising a portion of the sample, and a reaction mixture;
    amplifying the plurality of discrete sample portions to form a plurality of discrete processed sample portions including at least one discrete processed sample portion containing nucleic acid amplification reaction products;
    detecting fluorescence signals from the at least one of the plurality of discrete processed sample portions to determine a presence of the at least one target nucleic acid;
    determining the respective volumes of the plurality of discrete processed sample portions, wherein the determining the respective volumes comprises imaging the plurality of discrete processed sample portions; and
    estimating the number of copies-per-unit-volume of the at least one target nucleic acid in the sample based on the number of discrete processed sample portions determined to contain the at least one target nucleic acid therein.

2. The method of claim 1, wherein the plurality of discrete sample portions comprises discrete sample portions of a plurality of sizes.

3. The method of claim 1, wherein the plurality of discrete sample portions comprises discrete sample portions of substantially two different sizes.

4. The method of claim 1, wherein the plurality of discrete sample portions comprise discrete sample portions of substantially a plurality of predetermined sizes.

5. The method of claim 1, wherein each of the plurality of sample portions is at least partially surrounded by a medium that is at least substantially immiscible with the plurality of discrete sample portions.

6. The method of claim 5, wherein the medium that is substantially immiscible with the plurality of discrete sample portions comprises at least one selected from the group consisting of: a mineral oil, a silicone oil, a paraffin oil, a fluorinated fluid, a perfluorinated polyether.

7. The method of claim 1, wherein the plurality of discrete sample portions comprises porous beads.

8. The method of claim 1, wherein the plurality of discrete sample portions comprises magnetic beads.

9. The method of claim 8, further comprising magnetically focusing the magnetic beads within a flow stream of immiscible fluid in a flow cytometer.

10. The method of claim 1, wherein the amplifying includes a polymerase chain reaction.

11. A system for quantification of a target nucleic acid in a sample, the system comprising:
- an emulsion apparatus configured to form a plurality of discrete sample portions, each of the plurality of discrete sample portions comprising a portion of the sample, and a reaction mixture;
- an amplification apparatus configured to amplify the plurality of discrete sample portions to form a plurality of discrete processed sample portions including at least one discrete processed sample portion containing nucleic acid amplification reaction products;
- an excitation detection apparatus configured to detect fluorescence signals from the at least one of the plurality of discrete processed sample portions to determine a presence of the at least one target nucleic acid; and
- a processor configured to:
  - determine respective volumes of the plurality of discrete processed sample portions by imaging the plurality of discrete processed sample portions, and
  - estimate the number of copies-per-unit-volume of the at least one target nucleic acid in the sample based on the number of discrete processed sample portions determined to contain the at least one target nucleic acid therein.

12. The system of claim 11, wherein the excitation detection apparatus is further configured to determine the respective volumes of the plurality of discrete processed sample portions.

13. The system of claim 11, further comprising an optical imager configured to determine the respective volumes of the plurality of discrete processed sample portions.

14. The system of claim 11, wherein the emulsion apparatus is configured to form the plurality of discrete sample portions of a plurality of sizes.

15. The system of claim 11, wherein the emulsion apparatus is configured to form the plurality of discrete sample portions of substantially two different sizes.

16. The system of claim 11, wherein the emulsion apparatus is configured to form the plurality of discrete sample portions of substantially a plurality of predetermined sizes.

17. The system of claim 11, wherein each of the plurality of discrete sample portions is at least partially surrounded by a medium that is at least substantially immiscible with the plurality of discrete sample portions.

18. The system of claim 17, wherein the medium that is substantially immiscible with the plurality of sample portions comprises at least one selected from the group consisting of: a mineral oil, a silicone oil, a paraffin oil, a fluorinated fluid, a perfluorinated polyether.

19. The system of claim 11, wherein the plurality of discrete sample portions comprises porous beads.

20. The system of claim 11, wherein the plurality of discrete sample portions comprises magnetic beads.

21. The system of claim 20, wherein the excitation detection apparatus includes a flow cytometer configured to magnetically focus the magnetic beads within a flow stream of immiscible fluid.

22. The system of claim 11, wherein the amplification apparatus includes a polymerase chain reaction (PCR) instrument.

* * * * *